US012686701B2

(12) United States Patent
Hondal et al.

(10) Patent No.: US 12,686,701 B2
(45) Date of Patent: Jul. 21, 2026

(54) SUBSTITUTION OF HISTIDINE WITH 2-THIOHISTIDINE IN BIOACTIVE PEPTIDES

(71) Applicant: University of Vermont and State Agricultural College, Burlington, VT (US)

(72) Inventors: Robert J. Hondal, Burlington, VT (US); Kaelyn Jenny, Essex Junction, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 158 days.

(21) Appl. No.: 18/556,587

(22) PCT Filed: Apr. 22, 2022

(86) PCT No.: PCT/US2022/026025
§ 371 (c)(1),
(2) Date: Oct. 20, 2023

(87) PCT Pub. No.: WO2022/226360
PCT Pub. Date: Oct. 27, 2022

(65) Prior Publication Data

US 2024/0199687 A1 Jun. 20, 2024

Related U.S. Application Data

(60) Provisional application No. 63/178,485, filed on Apr. 22, 2021.

(51) Int. Cl.

| | |
|---|---|
| ***C07K 1/107*** | (2006.01) |
| ***A61K 8/64*** | (2006.01) |
| ***A61K 38/00*** | (2006.01) |
| ***A61Q 19/00*** | (2006.01) |
| ***C07K 1/04*** | (2006.01) |
| ***C07K 1/06*** | (2006.01) |
| ***C07K 1/14*** | (2006.01) |
| ***C07K 5/068*** | (2006.01) |
| ***C07K 5/09*** | (2006.01) |
| ***C07K 7/06*** | (2006.01) |

(52) U.S. Cl.
CPC .............. *C07K 1/1075* (2013.01); *A61K 8/64* (2013.01); *A61Q 19/00* (2013.01); *C07K 1/042* (2013.01); *C07K 1/063* (2013.01); *C07K 1/1077* (2013.01); *C07K 1/14* (2013.01); *C07K 5/06086* (2013.01); *C07K 5/0815* (2013.01); *C07K 7/06* (2013.01); *A61K 38/00* (2013.01)

(58) Field of Classification Search
CPC ........ C07K 1/1075; C07K 1/042; A61K 8/64; A61K 38/00; A61Q 19/00
See application file for complete search history.

(56) References Cited

U.S. PATENT DOCUMENTS

2012/0330029 A1 12/2012 Erdelmeier et al.

FOREIGN PATENT DOCUMENTS

EP 0142387 A1 5/1985

OTHER PUBLICATIONS

Pubchem, SID 33849327, https://pubchem.ncbi.nlm.nih.gov/substance/33849327, Dec. 5, 2007, 5 pages.
Zwick III, C.R., et al., Modular Chemoenzymatic Synthesis of GE81112 B1 and Related Analogues Enables Elucidation of Its Key Pharmacophores, Journal of the American Chemical Society, Jan. 8, 2021, vol. 143, No. 3, pp. 1673-1679.
Maggiora, L.L., et al., L-2-thiol-histidine: Introduction of conformational constraints into peptides via thioether linkage, Tetrahedron Letters, 1990, vol. 31, No. 20, pp. 2837-2840.
Jenny, K.A., et al., We have a POA signed by Corine as Director of Office of Technology and Commercialization. Googling, I see she is Director of UVM Innovations (formally [sic] the Office of Technology Commercialization), Journal of Peptide Science, May 18, 2021, vol. 27, No. 10, article e3339, 12 pages.

*Primary Examiner* — Anna Pagonakis
(74) *Attorney, Agent, or Firm* — Hodgson Russ LLP

(57) ABSTRACT

Presented is a method to incorporate 2-thiohistidine (2-thio-His) into a peptide. Also provided are peptides incorporating 2-thioHis, compositions, and methods of using the peptides incorporating 2-thioHis. The methods may be methods for scavenging metals and/or radicals or reducing oxidative stress. 2-thioHis has the following structure

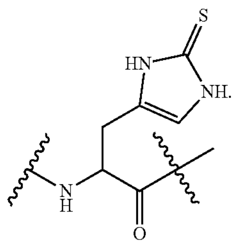

18 Claims, 17 Drawing Sheets

Specification includes a Sequence Listing.

ergothioneine 2-thiohistidine carnosine

GHK-tripeptide

A

B ergothioneine 2-thioHis in a peptide = new antioxidant activity + Cu binding

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

His Gly Pro Leu Gly Pro Leu
1               5
```

SUBSTITUTION OF HISTIDINE WITH 2-THIOHISTIDINE IN BIOACTIVE PEPTIDES

CROSS REFERENCE TO RELATED APPLICATION

This application claims priority to U.S. Provisional Application No. 63/178,485, filed on Apr. 22, 2021, the disclosure of which is incorporated herein by reference.

STATEMENT REGARDING FEDERALLY SPONSORED RESEARCH

This invention was made with government support under grant no. HL141146 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 22, 2022, is named "073777_00094_SEQ_ID.txt", and is 481 bytes in size.

BACKGROUND OF THE DISCLOSURE

Ergothioneine (EGT) is the betaine of 2-thiohistidine (2-thioHis) and may be the last undiscovered vitamin. EGT is produced by fungi and mycobacteria and has been shown to be a potent antioxidant compound in vitro, but its precise biological function is unknown. Humans and other animals obtain EGT by ingesting food and accumulate it in target tissues, such as red blood cells, by the use of a specific cation transporter. EGT also chelates metals, especially Cu(II), and prevents the metal from undergoing redox cycling reactions that generate reactive oxygen species (ROS) that damage biological macromolecules.

EGT cannot be incorporated into a peptide since the α-nitrogen is trimethylated (FIG. 1). There is only one other reported instance of incorporating 2-thioHis into a peptide. This is most likely due to lack of commercial availability and the problems of protection/deprotection of the thione sulfur atom, which was previously reported, in which a 4-methylbenzyl (Meb) protecting group was used.

SUMMARY OF THE DISCLOSURE

Described herein is a method for the incorporation of 2-thioHis into peptides in which the thione is unprotected. This decision was based upon the reported low reactivity of EGT with 5,5'-dithiobis(2-nitrobenzoic acid) (DTNB), a very electrophilic disulfide. Described is the synthesis of 2-thioHis analogues of carnosine (βAH), GHK-tripeptide, and HGPLGPL (SEQ ID NO:1). Each of these peptides contain a histidine (His) residue and possesses biological activity. These data show that substitution of His with 2-thioHis imparts strong antioxidant, radical scavenging, and copper binding properties to the peptide. Notably, it was found that the 2-thioHis analogue of GHK-tripeptide was able to completely quench the hydroxyl and ABTS radicals in various assays, and its antioxidant capacity was significantly greater than would be expected based on the antioxidant capacity of free 2-thioHis.

In an aspect, the present disclosure provides a method for preparing modified peptides comprising:

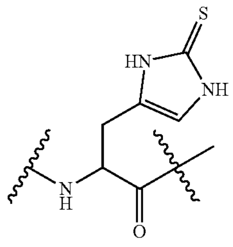

(e.g.,

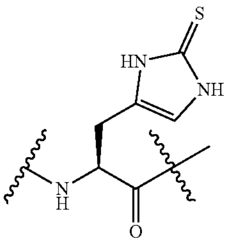

), the amino acid of which may be referred to as 2-thioHis. The peptides of the present disclosure may be prepared via solid phase peptide synthesis (SPPS) using fluorenylmethoxycarbonyl-based (Fmoc-based) chemistries.

A method of the present disclosure comprises utilizing SPPS, where

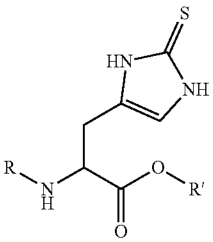

(e.g.,

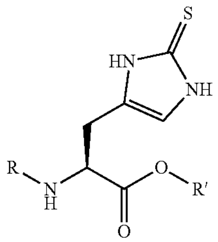

), is reacted with a nucleophilic group of a peptide covalently attached to a resin, an amino acid covalently attached to a resin, peptidomimetic covalently attached to a resin, or to a resin or with a carbocation of a resin. R is an amine protecting group, such as, for example, Fmoc and R' is H or a group formed from a carbodiimide (e.g., the —OR' is an activated ester). Aside from the N-terminal protecting group, 2-thioHis has no other protecting groups. Specifically, the thione of 2-thioHis is not protected during reaction (e.g., coupling) of 2-thioHis. The nucleophilic group may be the N-terminal amine of a peptide covalently attached to a resin, of a peptidomimetic covalently attached to a resin, of an amino acid covalently attached to a resin, or of a resin. In other embodiments, the nucleophilic group is a hydroxide of a resin, of an amino acid derivative covalently attached to a resin (e.g., a depsipeptide-based amino acid derivative), or of peptidomimetic attached to a resin. Following attachment (e.g., coupling) of 2-thioHis to the peptide covalently attached to a resin, amino acid covalently attached to a resin, peptidomimetic covalently attached to a resin, or resin, the amine protecting group of the 2-thioHis may be removed from the amine group of 2-thioHis and additional amino acids may be sequentially added to the peptide chain using standard SPPS techniques known in the art. The method does not comprise using a thione-protected derivative of 2-thioHis:

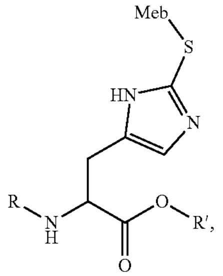

where Meb is p-methylbenzyl.

In an aspect, the present disclosure provides modified peptides. Examples of modified peptides are provided herein.

In an aspect, the present disclosure provides compositions. The composition may comprise a modified peptide of the present disclosure and a pharmaceutically acceptable carrier.

In an aspect, the present disclosure provides methods of using modified peptides of the present disclosure. The method may be a method for scavenging metals and/or radicals or reducing oxidative stress.

BRIEF DESCRIPTION OF THE FIGURES

For a fuller understanding of the nature and objects of the disclosure, reference should be made to the following detailed description taken in conjunction with the accompanying figures.

FIG. 9 shows absorbance spectral scan of carnosine and thioHcarnosine as a function of $CuCl_2$ concentration. (A) Absorbance scan of carnosine (10 mM) as $CuCl_2$ is titrated from 0 mM (black line) to 30 mM (light grey line). The absorbance at 610 nm increases as $CuCl_2$ is added to the peptide and then levels off. (B) Absorbance scan of thioHcarnosine (100 μM) as $CuCl_2$ is titrated from 0 μM (black line) to 250 μM (light beige line). The absorbance at 255 nm decreases as $CuCl_2$ is added to the peptide, while the absorbance at 220 nm increases. The tailing absorbance at 300 nm also increases as $CuCl_2$ is titrated in.

2-thioHis and DPPH assay UV-Vis absorbance spectra. C) HGPLGPL and DPPH assay UV-Vis absorbance spectra. D) thioHGPLGPL and DPPH assay UV-Vis absorbance spectra. E) Carnosine and DPPH assay UV-Vis absorbance spectra. F) thioHcarnosine and DPPH assay UV-Vis absorbance spectra.

Figure 18:
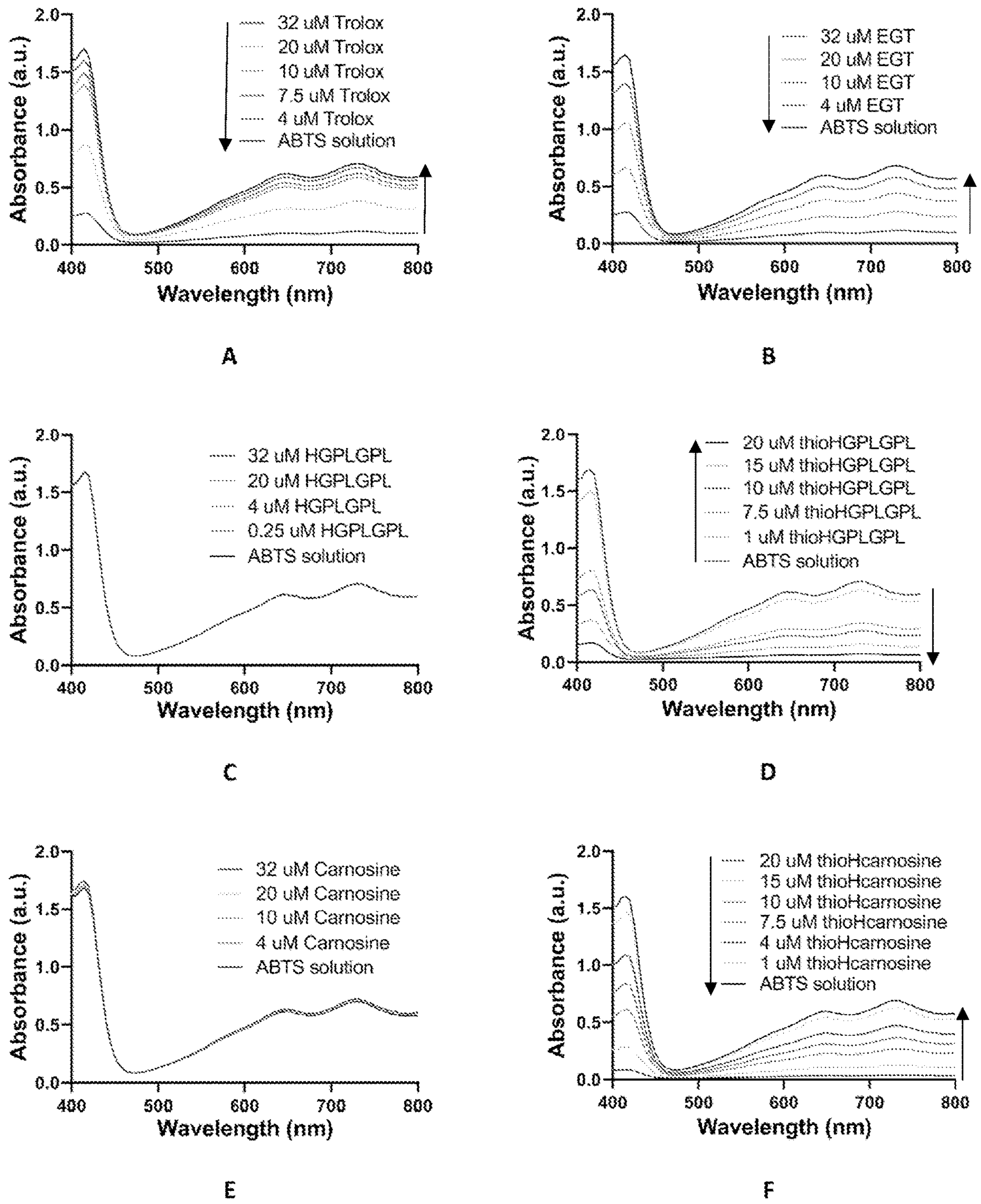

FIG. 18 shows UV/Vis spectra showing ABTS radical scavenging activity for all peptides and compounds tested. A) Trolox and ABTS assay UV-Vis spectra. B) EGT and ABTS assay UV-Vis spectra. C) HGPLGPL and ABTS UV-Vis assay spectra. D) thioHGPLGPL and ABTS UV-Vis assay spectra. E) Carnosine and ABTS assay UV-Vis spectra. F) thioHcarnosine and ABTS assay UV-Vis spectra.

Figure 19:
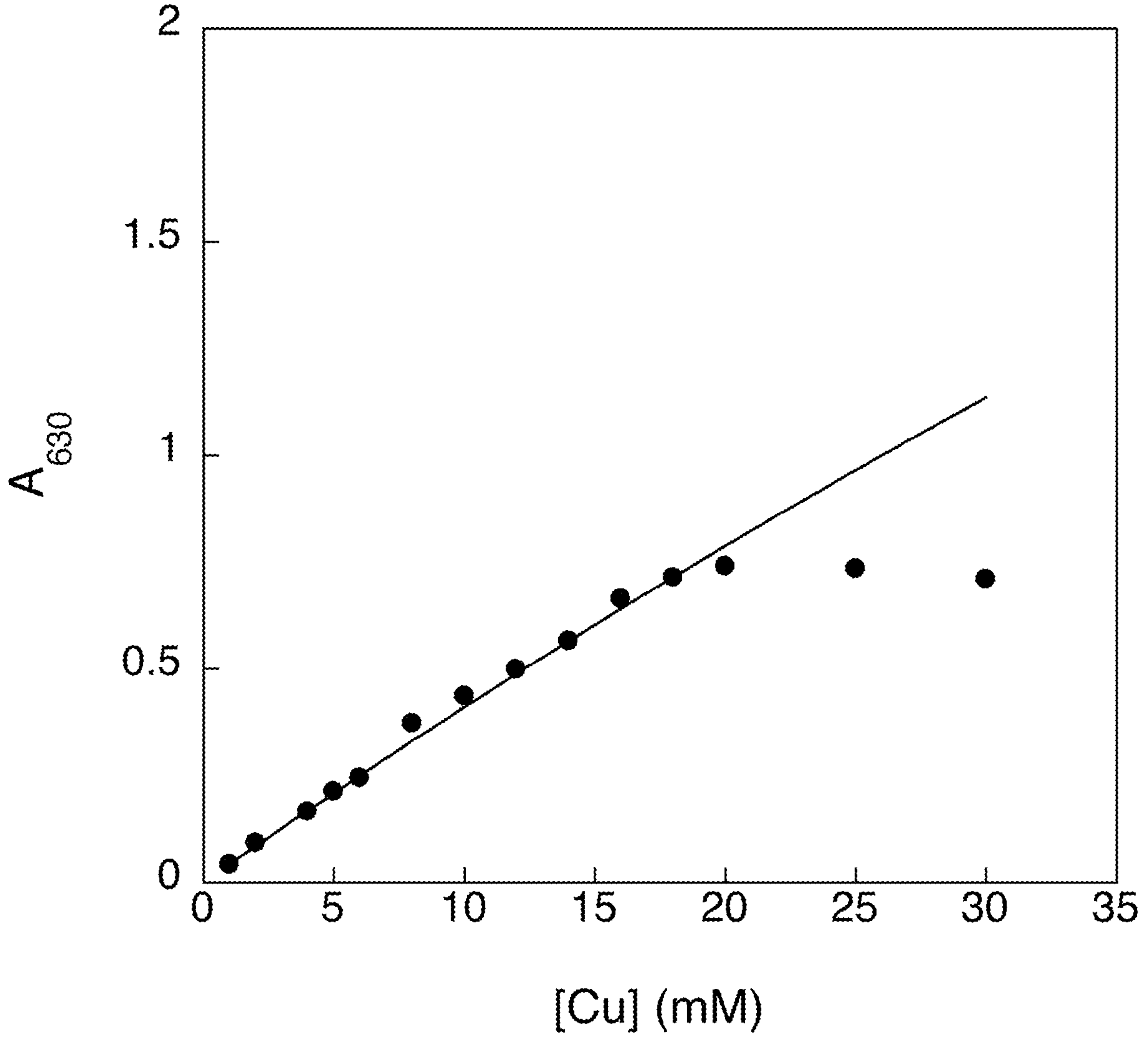

FIG. 19 shows titration of 10 mM carnosine with $CuCl_2$. The change in absorbance at 630 nm versus the $CuCl_2$ concentration was plotted. The data was then fit to the equation $\Delta A630=\varepsilon_{complex}[Cu]/K_A+[Cu]$ where $K_A$ is the association constant for the complex and $\varepsilon_{complex}$ is the extinction coefficient for the carnosine·copper complex. The fit was determined by using a double reciprocal plot of $1/\Delta A630$ versus 1/[Cu] in order to derive the values of $K_A$ and $\varepsilon_{complex}$. The resulting fit of the double reciprocal plot for the linear portion of the data is shown in the figure.

DETAILED DESCRIPTION OF THE DISCLOSURE

Although claimed subject matter will be described in terms of certain embodiments/examples, other embodiments/examples, including embodiments/examples that do not provide all of the benefits and features set forth herein, are also within the scope of this disclosure. Various structural, logical, process and step changes may be made without departing from the scope of the disclosure.

All ranges provided herein include all values that fall within the ranges to the tenth decimal place, unless indicated otherwise.

In this application, the use of the singular form encompasses the plural and vice versa.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent, trivalent, and the like, radicals). Illustrative examples of groups include:

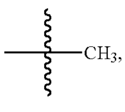, 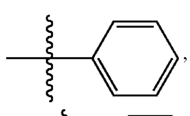, 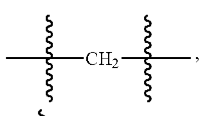, and

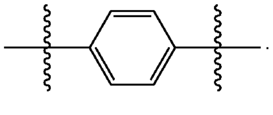.

Amino acids may be referred to herein by either their commonly known three letter symbols or by the one-letter symbols recommended by the IUPAC-IUB Biochemical Nomenclature Commission.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. In an example, about refers to ±1%, ±2%, ±3%, ±4%, ±5%, ±6%, ±7%, ±8%, ±9%, ±10%, ±15%, or ±20%.

Described herein is a method for the incorporation of 2-thioHis into peptides in which the thione is unprotected. This decision was based upon the reported low reactivity of EGT with 5,5'-dithiobis(2-nitrobenzoic acid) (DTNB), a very electrophilic disulfide. Described is the synthesis of 2-thioHis analogues of carnosine (βAH), GHK-tripeptide, and HGPLGPL (SEQ ID NO:1). Each of these peptides contain a histidine (His) residue and possesses biological activity. These data show that substitution of His with 2-thioHis imparts strong antioxidant, radical scavenging, and copper binding properties to the peptide. Notably, it was found that the 2-thioHis analogue of GHK-tripeptide was able to completely quench the hydroxyl and ABTS radicals in various assays, and its antioxidant capacity was significantly greater than would be expected based on the antioxidant capacity of free 2-thioHis.

In an aspect, the present disclosure provides a method for preparing modified peptides comprising:

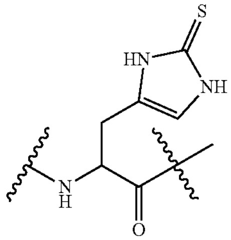 (e.g., 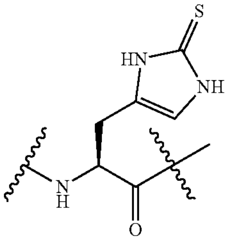), the amino acid of which may be referred to as 2-thioHis. The peptides of the present disclosure may be prepared via solid phase peptide synthesis (SPPS) using fluorenylmethoxycarbonyl-based (Fmoc-based) chemistries.

A method of the present disclosure comprises utilizing SPPS, where

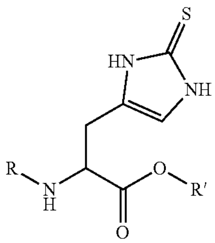 (e.g., 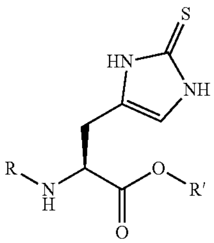)

is reacted with a nucleophilic group of a peptide covalently attached to a resin, an amino acid covalently attached to a resin, peptidomimetic covalently attached to a resin, or to a resin or with a carbocation of a resin. R is an amine protecting group, such as, for example, Fmoc and R' is H or a group formed from a carbodiimide (e.g., the —OR' is an activated ester). Aside from the N-terminal protecting group, 2-thioHis has no other protecting groups. Specifically, the thione of 2-thioHis is not protected during reaction (e.g., coupling) of 2-thioHis. The nucleophilic group may be the N-terminal amine of a peptide covalently attached to a resin, of a peptidomimetic covalently attached to a resin, of an amino acid covalently attached to a resin, or of a resin. In other embodiments, the nucleophilic group is a hydroxide of a resin, of an amino acid derivative covalently attached to a resin (e.g., a depsipeptide-based amino acid derivative), or of peptidomimetic attached to a resin. Following attachment (e.g., coupling) of 2-thioHis to the peptide covalently attached to a resin, amino acid covalently attached to a resin, peptidomimetic covalently attached to a resin, or resin, the amine protecting group of the 2-thioHis may be removed from the amine group of 2-thioHis and additional amino acids may be sequentially added to the peptide chain using standard SPPS techniques known in the art. The method does not comprise using a thione-protected derivative of 2-thioHis:

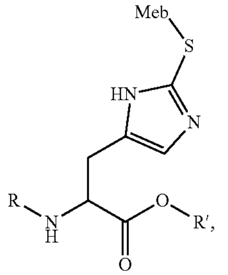

where Meb is p-methylbenzyl.

Various amino acids may be used in a method of the present disclosure. Examples of amino acids include, but are not limited to, canonical amino acids, non-canonical amino acids, amino acid derivatives, and the like, and combinations thereof.

Various resins may be used. For example, non-limiting examples of resins are Rink amide resins, PAL resins, Sieber Amide resins, Wang resins, trityl resins, chlorotrityl resins, and the like. Other resins are known in the art and are considered within the scope of the present disclosure.

In various embodiments, to attach (e.g., couple) 2-thioHis to an amino acid covalently attached to a resin, peptide covalently attached to a resin, peptidomimetic covalently attached to a resin, or resin, a reaction mixture is formed comprising a solvent (e.g., dimethylformamide (DMF)), 2-thioHis, and an activator (e.g., a carbodiimide), such that an activated ester of 2-thioHis is formed. The reaction mixture is then contacted with a nucleophilic group (e.g., amine) of the peptide covalently attached to a resin, amino acid covalently attached to a resin, peptidomimetic covalently attached to a resin, or resin, whereby the nucleophilic group reacts with the activated 2-thioHis, covalently attaching it to the peptide covalently attached to a resin, amino acid covalently attached to a resin, peptidomimetic covalently attached to a resin, or resin. This may be repeated prior to amine deprotection of the 2-thioHis.

Various activators may be used. For example, activator may be a carbodiimide. For example, suitable carbodiimides include, but are not limited to, diisopropylcarbodiimide (DIC), 1-hydroxybenzotriazole (HOBt), 1-hydroxy-7-azabenzotriazole (HOAt), 2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxide hexafluorophosphate (HATU), and the like, and combinations thereof. The carbodiimides may be used to form the carbodiimide group of R'.

When attaching 2-thioHis to a chlorotrityl or trityl resin, a reaction mixture may be formed using 2-thioHis, a base (e.g., N-methylmorpholine (NMM)) and a solvent (e.g., dichloromethane (DCM)) and the reaction mixture is contacted with the resin, whereby the 2-thioHis is covalently attached (e.g., coupled) to the resin. The resin may be capped prior to coupling of additional amino acids to the 2-thioHis covalently attached to the resin with methoxy groups. "Capping" refers to contacting a free amine or other nucleophilic group (e.g., —SH or —OH) with a reagent (e.g., acetic anhydride) such that the amine or other nucleophilic group are rendered inert. For example, an amine may be capped by contacting the amine with acetic anhydride, whereby the amine is acylated via chemical reaction with the acetic anhydride.

The method may comprise further one or more additional steps. For example, the method further comprises removing the amine protecting group from the amine of:

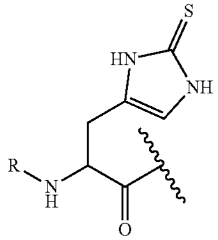

such that additional chemistry may be performed. When Fmoc is used as the amine protecting group, it may be removed from the amine by contacting the amine protected amino acid with a solution comprising piperidine and DMF. Additional chemistries includes, but are not limited to, addition of one or more amino acids (e.g., sequential coupling of one or more amino acids via SPPS), addition of a capping group or linking group, or the like. Examples of capping groups include, but are not limited to, acetyl groups, fatty acid groups (e.g., palmitoyl groups), vitamin groups (e.g., ascorbic acid groups). Examples of linking groups include, but are not limited to, succinyl groups, polyethylene glycol groups, and the like, and combinations thereof. In various embodiments, the capping group is covalently attached to the N-terminus of the peptide. In various embodiments, the N-terminal amino acid residue is 2-thioHis. In various examples, the capping group is covalently attached to the linking group. For example, the modified peptide having a free amine on the N-terminus may be contacted (e.g., reacted) with succinic acid (e.g., succinic acid activated using activated ester methods). Following attachment of the succinic acid to the modified peptide, a capping group, such as, for example, ascorbic acid may attached to the succinyl group of the modified peptide (using activated ester methods).

The method may further comprise cleaving the modified peptide from the solid support (e.g., resin). Methods of cleaving a peptide from resins are known in the art. For example, cleavage comprises contacting the modified peptide covalently attached to resin with a cleavage cocktail. For Fmoc-based chemistries, the cleavage cocktail may comprise trifluoroacetic acid (TFA). The cleavage cocktail may further comprise a silane (e.g., triisopropylsilane (TIS)) and water. Other cleavage cocktails include, but are not limited to, Reagent K, Reagent L, and Reagent R. Following cleavage, the solution comprising the cleaved modified peptide may be concentrated. Then, the modified peptide may be precipitated from the concentrated solution using, for example, cold, anhydrous ether. The precipitated peptide may be pelleted and then purified.

Methods to purify the modified peptides include using peptide purification methods known in the art. For example, purification may comprise utilizing high performance liquid chromatography (e.g., HPLC) or other similar methods. HPLC may be reverse-phase HPLC, where acetonitrile (with or without TFA) and water (with or without TFA) is the mobile phase. Various other mobile phases are known in the art and are within the scope of the present disclosure. The aqueous fractions containing the purified modified peptides may be concentrated using methods known in the art. For example, the aqueous fractions are lyophilized.

In an aspect, the present disclosure provides modified peptides. Examples of modified peptides are provided herein.

Various examples of modified peptides include:

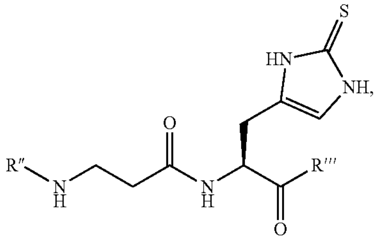

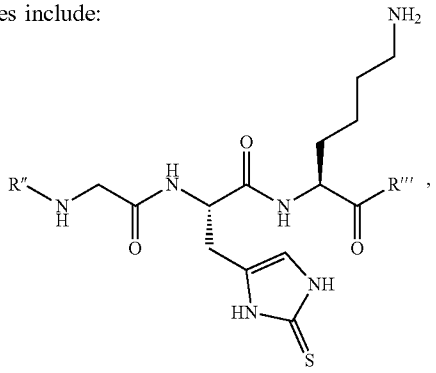

, or

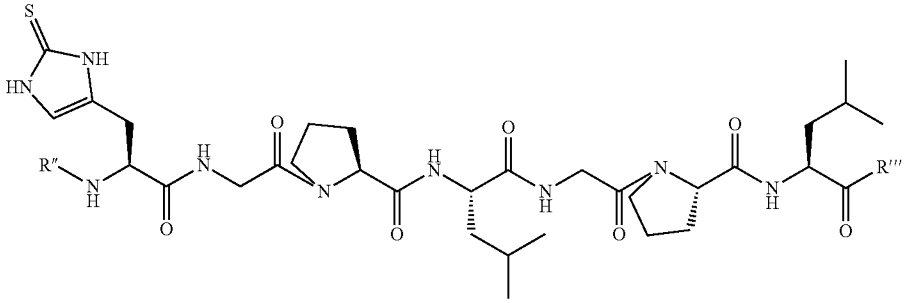

(SEQ ID NO:1, where His is replaced with 2-thioHis), where R" is a H, capping group, linking group, peptide, or linking group covalently bonded to a capping group and R"' is —OH, —$NH_2$, —OR"", where R"" is an alkyl group (e.g., methyl, ethyl, propyl, isopropyl, tert-butyl, or the like). In various examples, R"' is —OH, such as in the following examples:

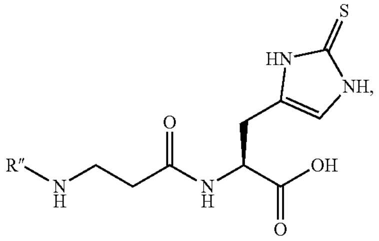

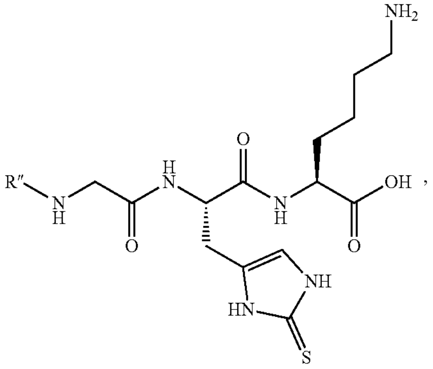

, or

-continued

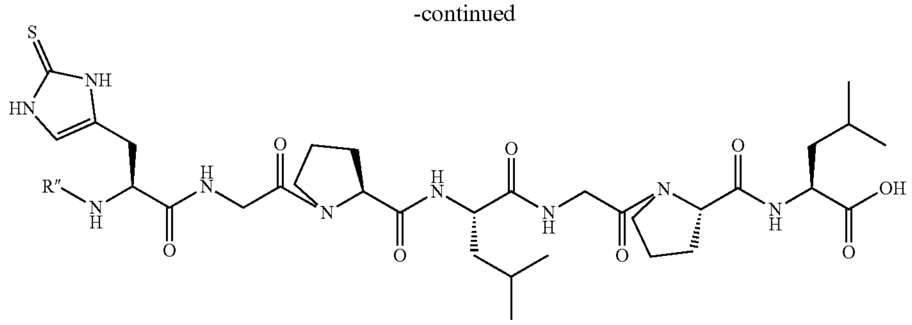

(SEQ ID NO:1, where His is replaced with 2-thioHis).

In various examples, a modified peptide has the following structure:

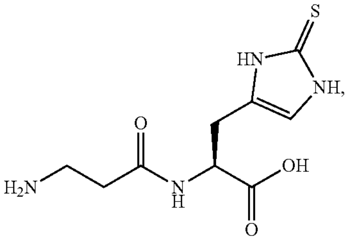

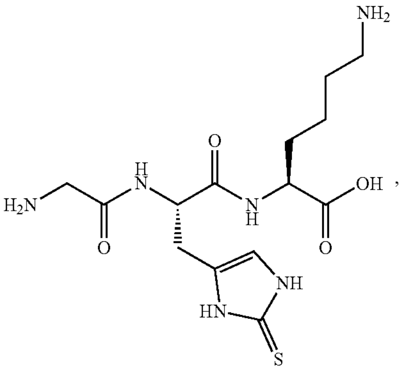

, or

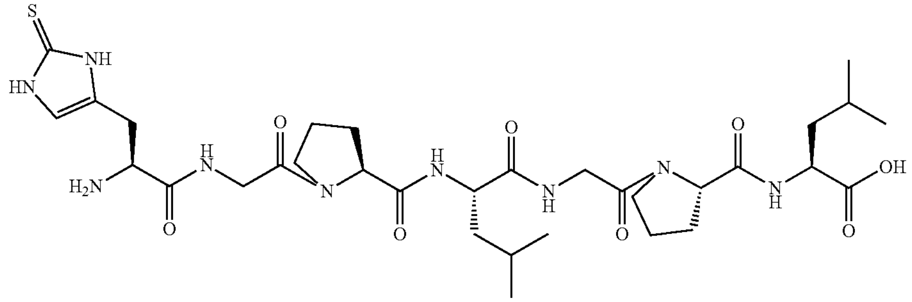

(SEQ ID NO:1, where His is replaced with 2-thioHis).

A modified peptide may be functionalized at the amine of the N-terminus. For example, the modified peptide is functionalized at the N-terminus with a capping group, a linking group, or a linking group covalently attached to a capping group. Examples of capping groups include, but are not limited to, acetyl groups, fatty acid groups (e.g., palmitoyl groups), vitamins (e.g., ascorbic acid), and the like. Examples of linking groups include, but are not limited to succinyl groups, polyethylene glycol groups, and the like, and combinations thereof.

In an aspect, the present disclosure provides compositions. The composition may comprise a modified peptide of the present disclosure and a pharmaceutically acceptable carrier.

The composition can comprise the modified peptides in a pharmaceutically acceptable carrier (e.g., carrier). The carrier can be an aqueous carrier suitable for administration to individuals including humans. The carrier can be sterile. The carrier can be a physiological buffer. Examples of suitable carriers include sucrose, dextrose, saline, and/or a pH buffering element (such as, a buffering element that buffers to, for example, a pH from pH 5 to 9, from pH 6 to 8, (e.g., 6.5)) such as histidine, citrate, or phosphate. Additionally, pharmaceutically acceptable carriers may be determined in part by the particular composition being administered. Accordingly, there are a wide variety of suitable formulations of pharmaceutical compositions of the present disclosure. Additional, non-limiting examples of carriers include solutions, suspensions, and emulsions that are dissolved or suspended in a solvent before use, and the like. The composition may comprise one or more diluents. Examples of diluents, include, but are not limited to distilled water, physiological saline, vegetable oil, alcohol, dimethyl sulfoxide, and the like, and combinations thereof. Compositions may contain stabilizers, solubilizers, suspending agents, emulsifiers, soothing agents, buffers, preservatives, and the like, and combinations thereof. Compositions may be sterilized or prepared by sterile procedure. A composition of the disclosure may also be formulated into a sterile solid preparation, for example, by freeze-drying, and may be used after sterilization or dissolution in sterile injectable water or other sterile diluent(s) immediately before use. Additional examples of pharmaceutically acceptable carriers include, but are not limited to, sugars, such as, for example, lactose, glucose, and sucrose; starches, such as, for example, corn starch and potato starch; cellulose, including sodium carboxymethyl cellulose, ethyl cellulose, and cellulose acetate; powdered tragacanth; malt; gelatin; talc; excipients, such as cocoa butter and suppository waxes; oils, such as, for example, peanut oil, cottonseed oil, safflower oil, sesame oil, olive oil, corn oil, and soybean oil; glycols, such as, for example, propylene glycol; polyols, such as, for example glycerin, sorbitol, mannitol, and polyethylene glycol; esters, such as, for example, ethyl oleate and ethyl laurate; agar; buffering agents, such as, for example, magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Additional non-limiting examples of pharmaceutically acceptable carriers can be found in: *Remington: The Science and Practice of Pharmacy* (2012) 22nd Edition, Philadelphia, PA. Lippincott Williams & Wilkins. For example, a composition comprises a modified peptide, and a sterile, suitable carrier for administration to individuals including humans—such as a physiological buffer such as sucrose, dextrose, saline, pH buffering (such as from pH 5 to 9, from pH 7 to 8, from pH 7.2 to 7.6, (e.g., 7.4)) element such as, for example, histidine, citrate, or phosphate. In various examples, the composition may be suitable for injection. Parenteral administration includes infusions and injections, such as, for example, intramuscular, intravenous, intraarterial, intraperitoneal, subcutaneous administration, and the like.

The compositions may be administered systemically. Compositions may be administered orally, may be administered parenterally, and/or intravenously. Compositions suitable for parenteral, administration may include aqueous and/or non-aqueous carriers and diluents, such as, for example, sterile injection solutions. Sterile injection solutions may contain anti-oxidants, buffers, bacteriostatic agents and solutes, which render the composition isotonic with the blood of the intended recipient. Aqueous and/or non-aqueous sterile suspensions may include suspending agents and thickening agents.

Nasal aerosol and inhalation compositions of the present disclosure may be prepared by any method in the art. Such compositions may include dosing vehicles, such as, for example, saline; preservatives, such as, for example, benzyl alcohol; absorption promoters to enhance bioavailability; fluorocarbons used in the delivery systems (e.g., nebulizers and the like; solubilizing agents; dispersing agents; or a combination thereof).

The compositions of the present disclosure may be administered systemically. The term "systemic" as used herein includes parenteral, topical, oral, spray inhalation, rectal, nasal, and buccal administration. The term "parenteral" as used herein includes subcutaneous, intravenous, intramuscular, intra-articular, intra-synovial, intrasternal, intrathecal, intrahepatic, intralesional, and intracranial administration. Preferably, the compositions are administered orally, intraperitoneally, or intravenously.

Examples of compositions include, but are not limited to, liquid solutions, such as, for example, an effective amount of a compound of the present disclosure suspended in diluents, such as, for example, water, saline or PEG 400. The liquid solutions described above may be sterile solutions. The compositions may comprise, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

In various embodiments, the composition may be a cosmetic. The cosmetic may be a skin care product. The skin care product may be a cream, lotion, foam, or the like. The skin care product may be suitable for topical application to an individual in need of treatment.

In an aspect, the present disclosure provides methods of using modified peptides of the present disclosure. The method may be a method for scavenging metals and/or radicals or reducing oxidative stress.

For example, a method may comprise contacting a solution comprising one or more metals (e.g., $Cu^{2+}$) and/or radicals (e.g., OH radicals, 2,2-diphenyl-1-picrylhydrazyl (DPPH) radicals, 2,2'-azino-di-[3-ethylbenzothiazoline sulfonate (ABTS) radicals, and the like, and combinations thereof). The one or more metals and/or radicals may bind to the modified peptide. For example, the modified peptide has the following structure:

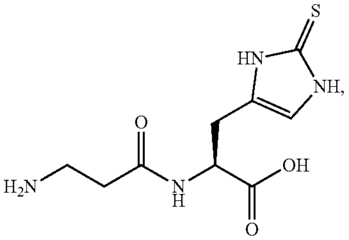

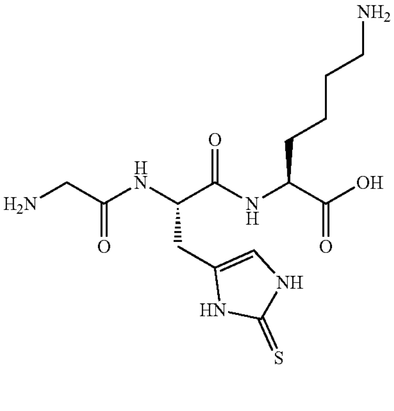

, or

-continued

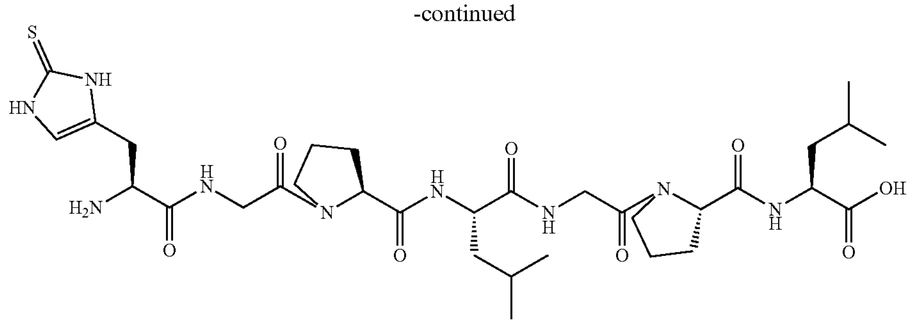

(SEQ ID NO:1, where His is replaced with 2-thioHis).

For example, a method may comprise administering a therapeutically effective amount of a modified peptide or composition comprising the modified peptide to an individual in need of treatment of oxidative stress. The administration may result in decreasing the amounts of free radicals, thereby reducing the oxidative stress on the individual. For example, the modified peptide has the following structure:

An individual in need of treatment may be a human or non-human mammal. Non-limiting examples of non-human mammals include cows, pigs, mice, rats, rabbits, cats, dogs, other agricultural animal, pet, service animals, and the like.

The steps of the method described in the various embodiments and examples disclosed herein are sufficient to carry out the methods of the present disclosure. Thus, in an embodiment, the method consists essentially of a combina-

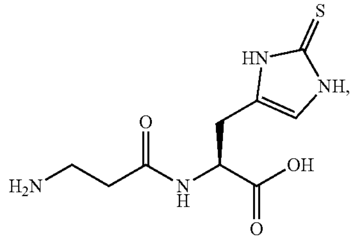

,

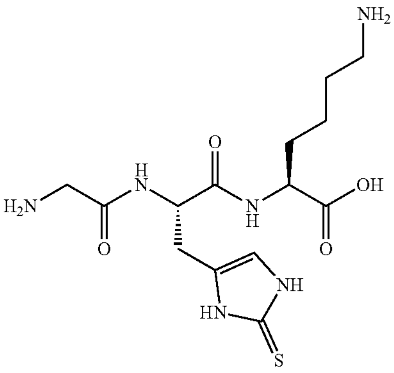

, or

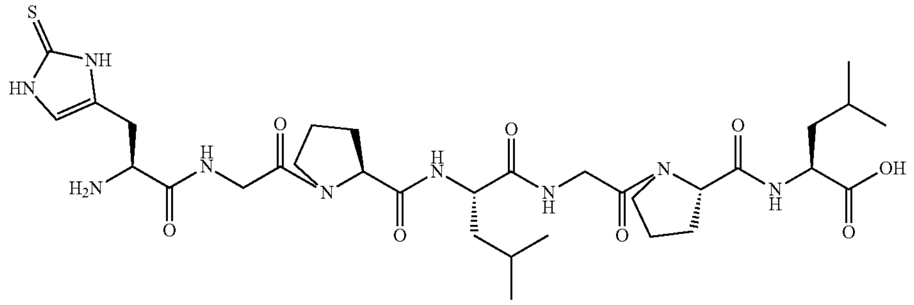

(SEQ ID NO:1, where His is replaced with 2-thioHis).

The phrase "therapeutically effective amount" is used herein to mean an amount sufficient to reduce by at least about 15 percent, preferably by at least 50 percent, more preferably by at least 90 percent, and most preferably prevents oxidative stress in the individual. Alternatively, a therapeutically effective amount is sufficient to cause an improvement in a clinically significant condition in the host.

In a method of the present disclosure, compositions may be administered by various routes. The compositions of the present disclosure may be administered systemically or orally.

tion of the steps of the methods disclosed herein. In another embodiment, the method consists of such steps.

The following Statements provide various examples of the present disclosure. They are not intended to be limiting in any way.

Statement 1. A method for making a modified peptide comprising: contacting a reaction mixture comprising a solvent (e.g., DMF, DCM, or the like),

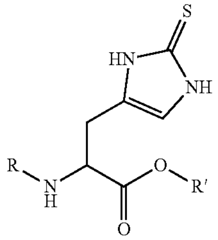
(e.g.,
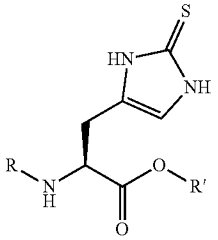
), optionally, an activator (e.g., a carbodiimide), and, optionally, a base (e.g., NMM), wherein R is an amine protecting group (e.g., Fmoc) and R' is an H or group formed from a carbodiimide, with: i) an amine group of a first amino acid covalently attached to a resin, peptide covalently attached to a resin, a peptidomimetic covalently attached to a resin, or resin, or ii) an alcohol of a first amino acid derivative attached to a resin, peptidomimetic attached to a resin, or resin, or iii) a carbocation of a resin; optionally, removing (e.g., deprotecting) the amine protecting group of the amine of

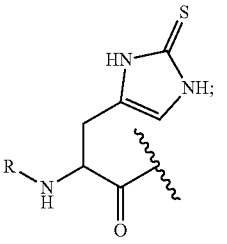

optionally, coupling a second amino acid, wherein the second amino acid is N-protected, to the unprotected amine; optionally, cleaving the N-protecting group of the second amino acid, optionally, repeating the coupling amino acid step and subsequent cleaving N-protecting group step; and cleaving the modified peptide from the resin, wherein the modified peptide is formed.

Statement 2. A method according to Statement 1, further comprising functionalizing the N-terminus of the modified peptide on resin with a capping group and/or a linking group prior to cleavage.

Statement 3. A method according to Statement 2, wherein the capping group is an acetyl group, a palmitoyl group, an ascorbic acid group, or the like.

Statement 4. A method according to Statements 2 or 3, wherein the linking group is a succinyl group, polyethylene glycol group, or the like, or a combination thereof.

Statement 5. A method according to any one of the preceding Statements, wherein the resin is a Rink resin, a Wang resin, a trityl resin, or a chlorotrityl resin.

Statement 6. A method according to any one of the preceding Statements, further comprising purifying the modified peptide.

Statement 7. A method according to any one of the preceding Statements, wherein the purifying is performed via HPLC.

Statement 8. A method according to any one of the preceding Statements, wherein the group formed from the activator (e.g., a carbodiimide) is formed from diisopropylcarbodiimide (DIC), 1-hydroxybenzotriazole (HOBt), 1-hydroxy-7-azabenzotriazole (HOAt), 2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxide hexafluorophosphate (HATU), or the like.

Statement 9. A method according to any one of the preceding Statements, wherein the amino acids are canonical amino acids, non-canonical amino acids, amino acid derivatives, or a combination thereof.

Statement 10. A modified peptide comprising:

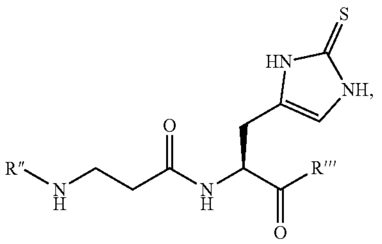
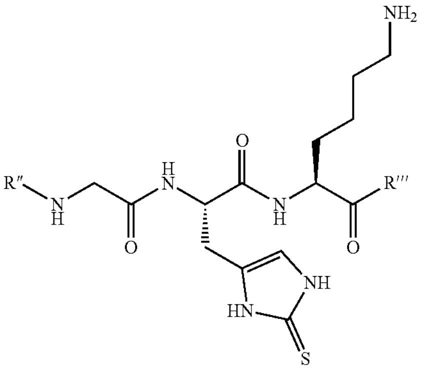
, or

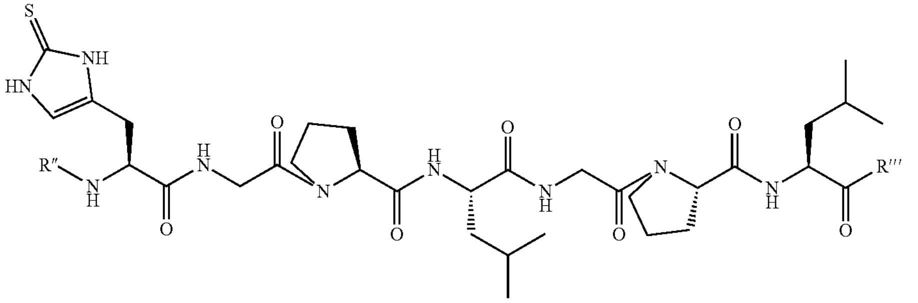

(SEQ ID NO:1, where His is replaced with 2-thioHis), wherein is a R" is H, capping group, linking group, peptide, or linking group covalently bonded to a capping group and R'" is —OH, —$NH_2$, —OR"", where R"" is an alkyl group.

Statement 11. A modified peptide according to Statement 10, wherein the modified peptide has the following structure:

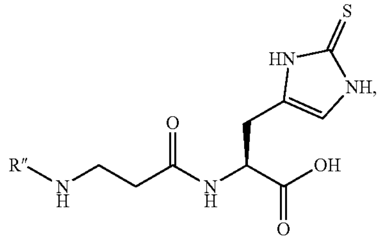

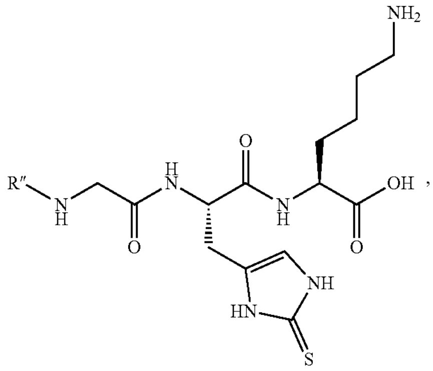

, or

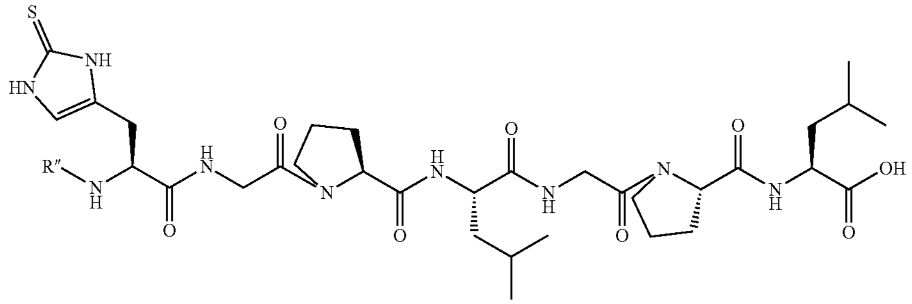

(SEQ ID NO:1, where His is replaced with 2-thioHis).

Statement 12. A modified peptide according to Statement 10 or 11, wherein the capping group is an acetyl group, a palmitoyl group, an ascorbic acid group, or the like.

Statement 13. A modified peptide according to any one of Statements 10-12, wherein the linking group is a succinyl group, polyethylene glycol group, or the like, or a combination thereof.

Statement 14. A modified peptide according to any one of Statements 10-13, wherein the modified peptide has the following structure:

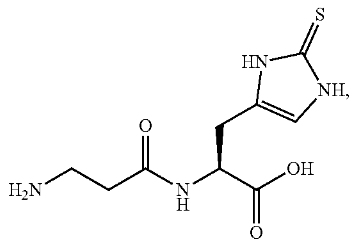

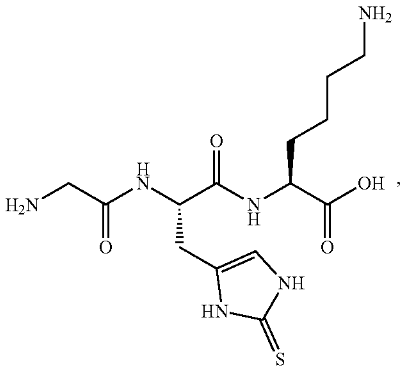

, or

-continued

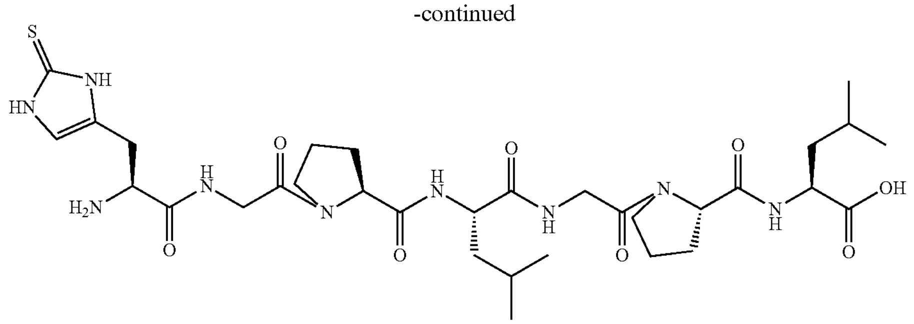

(SEQ ID NO:1, where His is replaced with 2-thioHis).

Statement 15. A composition comprising a modified peptide according to any one of Statements 10-14 and a pharmaceutically acceptable carrier.

Statement 16. A method for scavenging metals or radicals, comprising contacting a solution or medium comprising metals or radicals with a modified peptide according to any one of Statements 10-14 or a composition according to Statement 15, wherein the metals or radicals bind to the modified peptide.

Statement 17. A method for decreasing oxidative stress in an individual in need of treatment comprising administering to an individual a therapeutically effective amount of a modified peptide according to any one of Statements 10-14 or a composition of Statement 15, wherein the oxidative stress of the individual is decreased.

The following example is presented to illustrate the present disclosure. It is not intended to be limiting in any matter.

EXAMPLE

This example provides a description of methods, peptides, and uses of peptides of the present disclosure.

Although incorporation of an EGT-like moiety into a peptide would impart unique antioxidant and metal chelation properties to the peptide. This goal could be achieved by incorporating 2-thioHis, an EGT analogue, into a peptide and is possible because 2-thioHis has both α-amino and α-carboxylic acid groups that enable coupling to other amino acids. An advantage of such an approach is that peptides enable precise targeting to specific tissues and organelles and have defined hydrophobicity.

Figure 1:
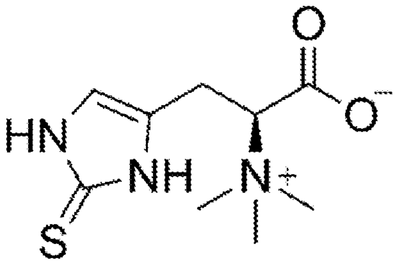
FIG. 1 shows structure of ergothioneine and 2-thiohistidine. EGT is the betaine (contains a trimethylated amine) of 2-thioHis.
Figure 1:
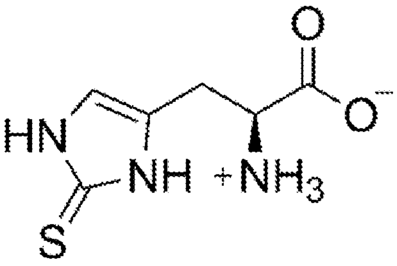
Figure 2:
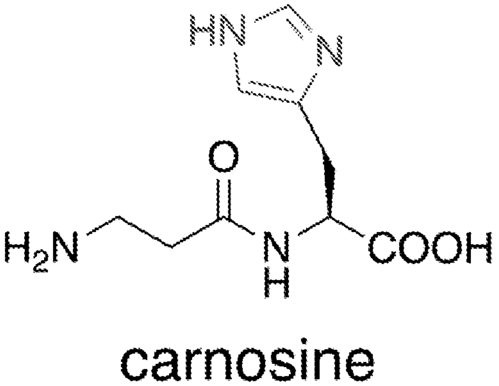
FIG. 2 shows naturally occurring His-containing peptides. Carnosine is a His-containing dipeptide found in the muscle of mammals where it has important antioxidant, metal chelation, and buffering properties. GHK-tripeptide is a matrikine from the extracellular matrix. It has a high affinity for Cu(II) and helps to prevent oxidative stress and is important for wound healing. Each has a His that can be replaced with 2-thioHis.
Figure 2:
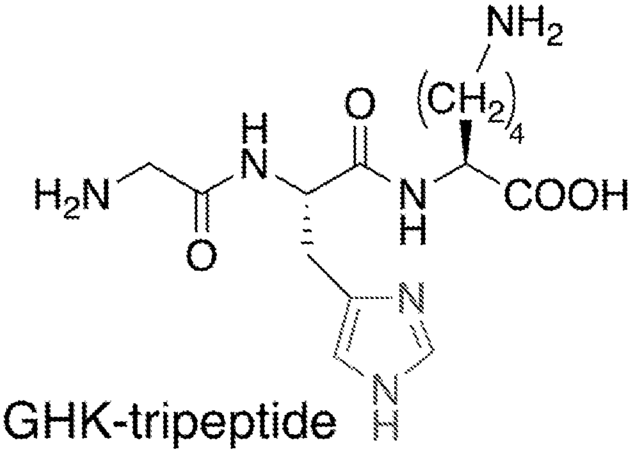

There are a number of bioactive His-containing peptides where replacement with 2-thioHis might be advantageous. These include, carnosine, GHK-tripeptide, GHTD-amide, histatins, and collagen-like peptides, some of which are depicted in FIG. 2.

Synthesis of the 2-thioHis analogs of bioactive peptides H-HGPLGPL-OH, H-GHK-OH, and H-βAH-OH (carnosine) is described herein. These His-containing peptides were chosen as targets because it has been reported that they each have antioxidant and/or metal chelating properties that could be enhanced by substitution with 2-thioHis.

Their antioxidant capacity were measured by measuring their ability to scavenge hydroxyl radicals and various organic radicals. Their ability to bind Cu(II) was quantified by using low temperature electron paramagnetic resonance (EPR) spectroscopy and ultraviolet-visible (UV-Vis) spectroscopy. These data suggest that the thione of 2-thioHis does not need to be protected in SPPS and that the resulting 2-thioHis-containing peptides have desirable antioxidant and metal chelation properties.

Materials and Methods

Materials. Solvents for peptide synthesis were purchased from Fisher Scientific (Pittsburgh, PA). 2,2'-azino-di-[3-ethylbenzthiazoline sulfonate (ABTS) was purchased from TCI America (Portland, Oregon). N-Fmoc amino acids were purchased from RS synthesis (Louisville, KY). 2-chlorotritylchloride resin (100-200 mesh, 1% DVB) was purchased from Novabiochem (St. Louis, MO). L-Carnosine was purchased from Acros Organics (Pittsburgh, PA). 1-[Bis(dimethylamino)methylene]-1H-1,2,3-triazolo[4,5-b]pyridinium 3-oxide hexafluorophosphate (HATU) was purchased from Oakwood Chemical (Estill, SC). All other chemicals were purchased from either Sigma-Aldrich (Milwaukee, WI), Acros Organics (Pittsburgh, PA), or Fisher Scientific (Pittsburgh, PA). Samples were ionized by ESI on a Thermo Q Exactive mass spectrometer (ThermoScientific, Waltham, MA). $^{1}$H-NMR and $^{13}$C-NMR spectra were recorded with a Bruker Advance III HD 500 MHz NMR spectrometer. All UV-Vis assays were performed on a Cary 50 UV-Vis spectrophotometer (Varian, Walnut Creek, CA). All EPR experiments were performed on a Bruker EMXplus EPR spectrometer (Billerica, MA). High-pressure liquid chromatography (HPLC) analysis of all samples was performed using a Shimadzu HPLC system with a Symmetry® C18 5-μm column from Waters Corp (Milford, MA) (4.6× 150 mm). For HPLC analysis, peptides were dissolved in water/HPLC-grade acetonitrile (5:1) to a concentration of 0.5 mM following lyophilization. The aqueous and organic phases were 0.1% TFA in distilled, deionized water (buffer A) and 0.1% TFA in HPLC-grade acetonitrile (buffer B), respectively. Beginning with 100% buffer A, buffer B was increased by 1% up to 50% over 50 min with a 1.4 mL/min gradient elution. Buffer B was then increased from 50% to 100% over 10 min. This method was used for analysis of each sample. Peptide elution was monitored via absorbance at both 214 nm and 254 nm.

Synthesis of L-2-thio-histidine. L-2-thiohistidine was synthesized according to a known procedure. This reaction works best when performed on 10 g or higher scale. Histidine (14 g, 66.8 mmol, 1.0 eq.) was dissolved in 134 mL of deionized water. After the His was fully dissolved, this solution was cooled in an ice bath at 0° C. Once the reaction was cooled, bromine (4.45 mL, 86.8 mmol, 1.3 eq.) was added resulting in a bright orange solution. After 6 min, Cys (24.3 g, 200.4 mmol, 3.0 eq.) was added to the reaction. The solution was stirred at 0° C.for 1 h. An oil bath was preheated to 95° C. After 1 h, 3-mercaptopropionic acid (34.9 mL, 400.7 mmol, 6.0 eq.) was added to the reaction and the reaction was transferred to the oil bath at 95° C. A condenser was attached to the reaction flask and the reaction was stirred for 18 h at 95° C., after which the reaction had turned dark brown. The reaction flask was removed from the oil bath and condenser was removed and the reaction flask was allowed to cool to room temperature. The aqueous solution was then extracted with ethyl acetate. The aqueous layer remained dark brown after extraction. The aqueous layer was transferred to a clean flask and placed in an oil bath preheated to 40° C. The pH of the solution was adjusted to 6.5 with 30% ammonia hydroxide to precipitate 2-thio-His. The reaction was chilled to allow complete precipitation. The off-white precipitate was filtered out of the reaction and washed with cold deionized water and ethanol. The precipitate was dried under high vacuum to give 5.04 g (26.9 mmol) of an off-white powder. The percent yield of this reaction was 40% which is consistent with known findings. Mass spectrometric (MS) analysis revealed a peak at 188.1 m/z. $^1$H-NMR ($D_2O$/DCl): δ 3.06-3.20 ((2H, (3.06 dd) (3.20 (dd)), 4.21 (1H, dd), 6.79 (1H, s); $^{13}$C-NMR ($D_2O$/DCl): δ 25.32, 51.82, 115.96, 123.23, 156.49, 170.38.

Figure 12:
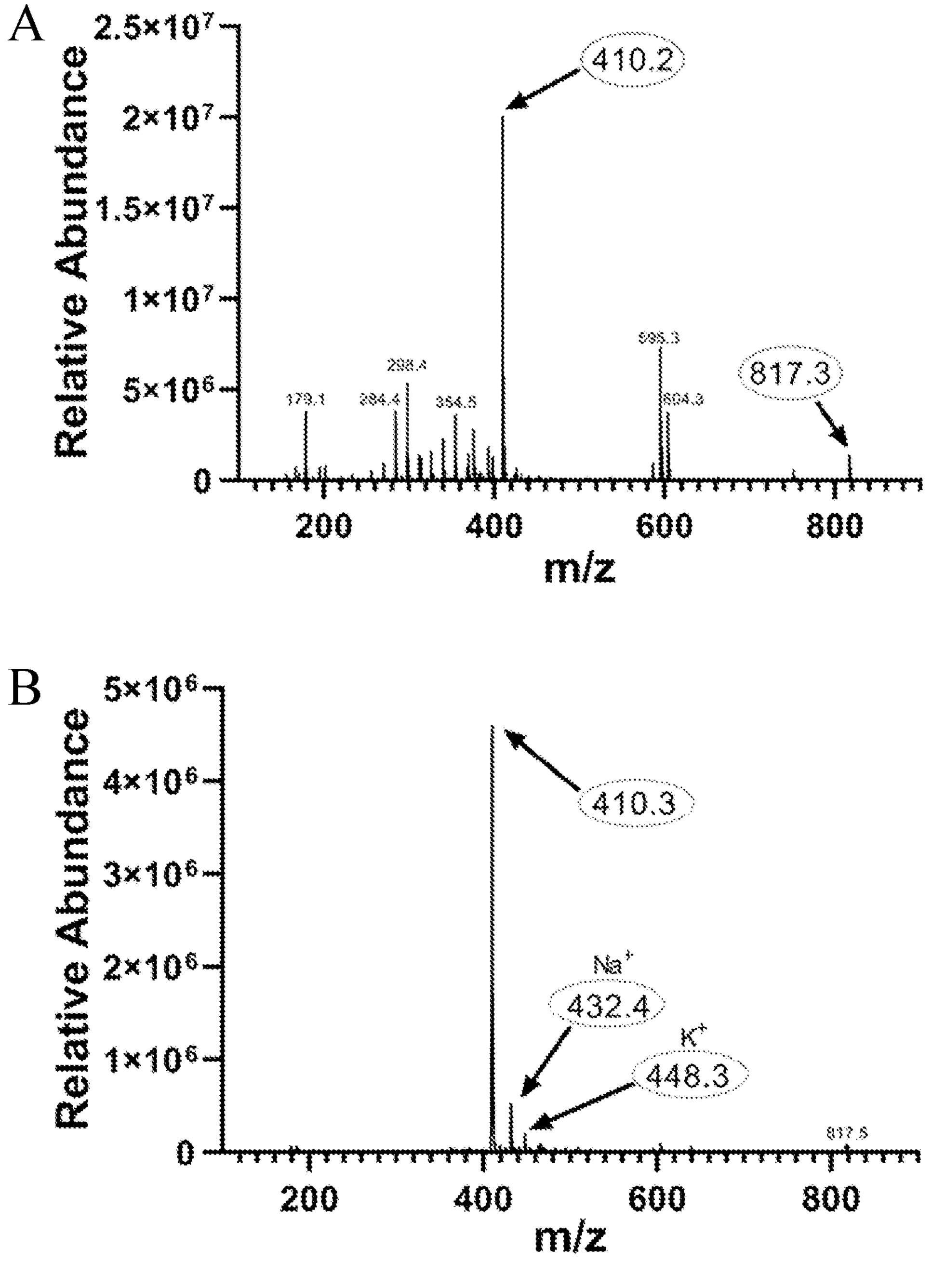
FIG. 12 shows mass chromatograms of N-Fmoc-2-thio-His disulfide before and after reduction with Asc. A) Mass spectrum of N-Fmoc-2-thioHis with disulfide at 817.3 m/z and the 2-thioHis plus N-Fmoc-2-thioHis disulfide at 595.3 m/z. B) Mass spectrum of N-Fmoc-2-thioHis with disulfide reduced by biphasic extraction of N-Fmoc-2-thioHis in ethyl acetate with aqueous 10 mM pH 4.2 ascorbate. The 595.3 m/z peak is gone and the 817.5 m/z peak is greatly reduced. The ability of ascorbate to reduce this disulfide indicates that the disulfide is very weak.

Addition of Fmoc protecting group to L-2-thioHis. N-Fmoc-L-2-thioHis was prepared using a standard procedure for the addition of fluorenylmethoxycarbonyl (Fmoc) protecting groups to amino acids. In a 250 mL round bottom flask, 2-thioHis (1.0 g) was added to 5-10 mL of deionized water to create a slurry. Triethylamine (TEA) (750 μL, 5.35 mmol, 1.0 eq.) was added to the amino acid slurry, and the reaction was stirred at room temperature. Fmoc N-hydroxysuccinimide ester (Fmoc-OSu) (1.99 g, 5.89 mmol, 1.1 eq.) was dissolved in 20-30 mL of acetonitrile and added to the amino acid slurry. A second eq. of TEA (750 μL) was added to the reaction along with acetonitrile and water to completely dissolve the 2-thioHis. The reaction was stirred for 2 h at room temperature and monitored by thin-layer chromatography (TLC). The reaction was quenched by acidifying with 20 mL of 1 N HCl. The reaction was extracted 3× with ethyl acetate followed by a back extraction of the ethyl acetate layer with water, 1 N HCl, and brine (1:1:1). The ethyl acetate solution was then dried with $MgSO_4$, filtered with a Büchner funnel, and roto-evaporated to dryness. The oil was dissolved in 10-20 mL of ethyl acetate with 1-2 mL of methanol. The addition of hexanes precipitated the N-Fmoc-2-thioHis derivative as a cream colored solid. The solid was purified by redissolving it in 10-20 mL of warm ethyl acetate and 1-2 mL of methanol, filtering the solution through a Büchner funnel, and then reprecipitating the product with cold hexanes. The product was dried under high vacuum and used without further purification. Mass spectrometric analysis showed a dominant peak at 410 m/z for the product as well as smaller peaks for the $Na^+$ adduct (M+23) at m/z 432 and the $K^+$ adduct (M+39) at m/z 448. $^1$H-NMR (MeOD): δ 2.88 (dd, 1H), 3.08 (dd, 1H), 4.22 (t, 1H), 4.35 (d, 2H), 4.43 dd, 1H), 6.60 (s, 1H), 7.32 (t, 2H), 7.40 (t, 2H), 7.65 (d, 2H), 7.80 (d, 2H); $^{13}$C-NMR (MeOD) δ 26.77, 53.06, 66.61, 119.49, 124.81, 126.78, 127.38, 141.16, 143.76, 143.83, 157.00, 172.87. An average yield was 82.5%. We note that that the MS of one of the reactions showed either a mixed disulfide between Fmoc-2-thioHis and 2-thioHis or a symmetrical disulfide with Fmoc-2-thioHis (FIG. 12). This disulfide could be eliminated by redissolving the product in ethyl acetate and extracting with 10 mM ascorbate (Asc), pH 4.25 (FIG. 12). If this step was necessary, the yield was reduced significantly. The disulfide was only observed when addition of the Fmoc group to 2-thioHis did not go to completion.

Peptide synthesis. All His-containing peptides (H-βAH-OH, H-HGPLGPL-OH, and H-GHK-OH) were synthesized according to standard SPPS protocols on a 0.1-mmol scale using a glass vessel shaken with a model 75 Burrell wrist action shaker. 300 mg of 2-chlorotrityl chloride resin (100-200 mesh, Chem-Impex) was used for each peptide. This resin was swelled in dichloromethane (DCM) for 20 min. The first amino acid was directly coupled to the resin using N-methylmorpholine (NMM)/DCM (2:98), shaking for 1 h. The resin was then capped using DCM/methanol/NMM (8:1:1). Subsequent amino acids were coupled using 0.2 mmol of Fmoc-protected amino acid, 0.2 mmol of HATU, and 1.8 mmol NMM in dimethylformamide (DMF), shaking for 1 h. Between amino acid couplings, the Fmoc-protecting group was removed by two 10-min washes with piperidine/DMF (2:8). The success of Fmoc removal and amino acid couplings were monitored qualitatively using a ninhydrin test. Peptides were cleaved from the resin with a cleavage cocktail consisting of trifluoroacetic acid (TFA)/triisopropylsilane (TIS)/water (96:2:2) for 1.5 h. Following cleavage, the resin was washed with DCM, and the volume of the cleavage solution was reduced by evaporation with argon gas. Each peptide was precipitated with cold, anhydrous ether. Centrifugation at 3000 rpm on a clinical centrifuge (International Equipment Co, Boston, MA) for 5 min pelleted the peptide. Peptides were dried under argon gas, then dissolved in a minimal amount of water/HPLC-grade acetonitrile (5:1), lyophilized, and used without further purification.

The 2-thioHis-containing peptides (H-βAthioH-OH (thio-Hcarnosine), H-thioHGPLGPL-OH, and H-GthioHK-OH) were synthesized with a similar protocol prior to coupling of 2-thioHis. For the coupling of 2-thioHis, 0.12 mmol of Fmoc-2-thioHis, 0.12 mmol of ethyl (hydroxyimino)cyanoacetate (EtCA), and 0.36 mmol of diisopropylcarbodiimide (DIC) was dissolved in DMF, added to the resin and shaken for 2 h. Double couplings were typically performed. When 2-thioHis was the first amino acid coupled to the resin, as was the case for H-βAthioH-OH, coupling was performed with 0.11 mmol of Fmoc-2-thioHis and 1.8 mmol NMM in DCM for 1 h. All subsequent coupling after 2-thioHis were performed with 0.2 mmol of Fmoc-protected amino acid, 0.2 mmol ETCA, and 0.6 mmol DIC in DMF for 1 h. The rest of the procedure is identical to the one used for the His-containing peptides. We note that the peptides containing 2-thioHis had a yellow color upon precipitation in ether and after lyophilization, while the His-containing peptides were white.

Figure 13:
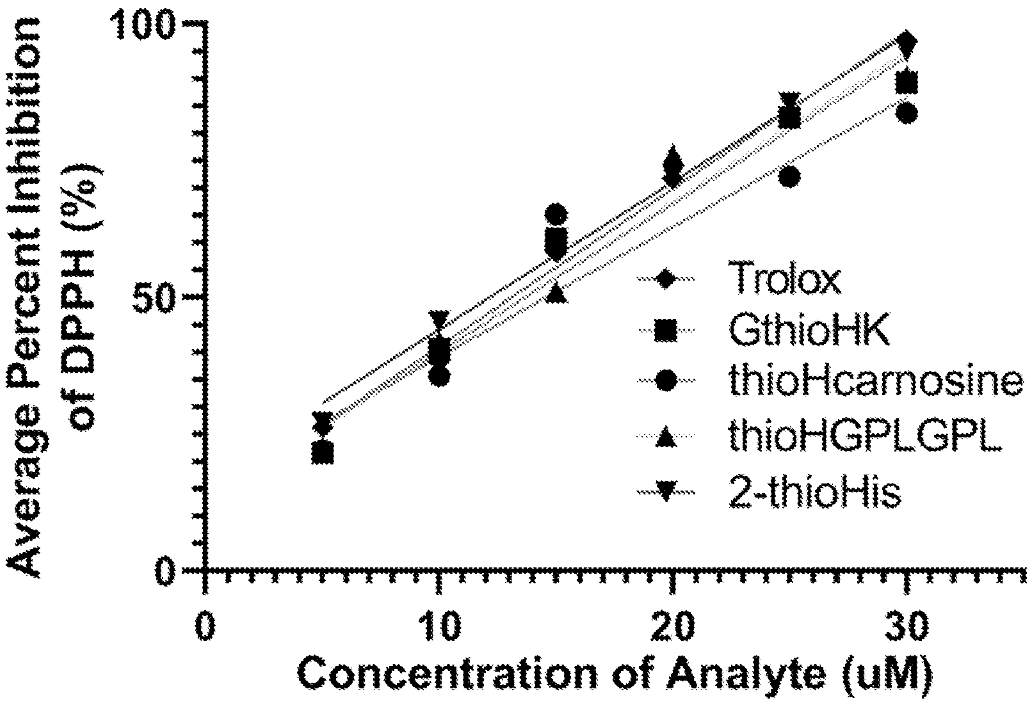
FIG. 13 shows TEAC value curves for 2-thioHis-containing peptide DPPH radical scavenging activity. Average percent inhibition of DPPH by 2-thioHis peptides, 2-thioHis, and Trolox. Each point is the average of three trials. Points are fitted with a linear regression line. All $R^2$ values for the linear regression are 90% or greater. The equations from the linear regression analyses were used to determine TEAC values for the DPPH assays.

Measurement of 2,2-diphenyl-1-picrylhydrazyl (DPPH) radical scavenging activity. DPPH activity assays were conducted according to procedures known in the art. A 1 mM stock solution of DPPH was prepared by dissolving DPPH in 95% ethanol. Peptide stock solutions were prepared at a concentration of 5 mM in 100 mM potassium phosphate buffer, pH 7.0 for each of the His- and 2-thioHis-containing peptides. 6-hydroxy-2,5,7,8-tetramethylchromane-2-carboxylic acid (Trolox) was used as a standard for antioxidant activity and a positive control. A 5 mM solution of Trolox in 100 mM potassium phosphate, pH 7.0 was prepared. A blank was prepared by mixing 600 μL of 95% ethanol with 400 μL of 100 mM potassium phosphate, pH 7.0 in a cuvette. This solution was used to blank the spectrophotometer from 200-800 nm. In each sample, a 60:40 ratio of ethanol:buffer was maintained. To test the ability of Trolox and the different peptides to reduce DPPH, 50 μM DPPH was combined with different concentrations of peptide or Trolox ranging from 5 μM to 500 μM and the total volume of each sample was adjusted to 1 mL with buffer and ethanol. The samples were allowed to incubate at room temperature in the dark for 15 min, after which each sample was scanned and changes in the absorbance at 517 nm were monitored. Trials were run in triplicate for each of the peptides and Trolox. For every trial, one sample was prepared with only 50 μM DPPH (no peptide or Trolox) to serve as a control. The percentage of inhibition of DPPH oxidation was calculated using Equation 1:

$$DPPH \text{ scavenging } (\%) = \frac{A_{control} - A_{sample}}{A_{control}} \times 100 \quad \text{Eq. 1}$$

where $A_{control}$ is the absorbance of the control (DPPH and buffer only) and $A_{sample}$ is the absorbance at 517 nm of the test peptide/standard. A Trolox calibration curve was prepared with concentrations ranging from 5-50 μM (FIG. 13). Similar curves were prepared for each of the peptides (FIG. 13). These curves were used to calculate Trolox equivalent antioxidant capacity (TEAC) values for each of the peptides by calculating the ratio of peptide to Trolox to achieve the same percent reduction of DPPH.

Figure 14:
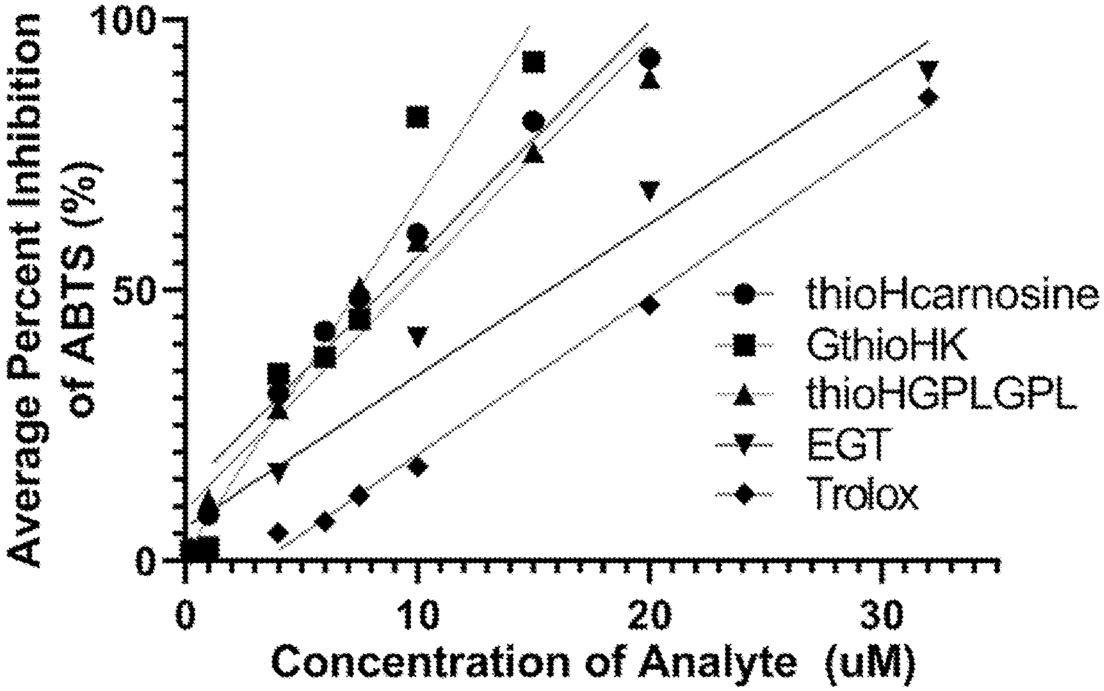
FIG. 14 shows TEAC value curves for 2-thioHis-containing peptide ABTS radical scavenging activity. Average percent inhibition of ABTS by 2-thioHis-containing peptides, EGT, and Trolox. Each point is the average of three trials. Points are fitted with a linear regression line. All $R^2$ values for the linear regression are 95% or greater. The equations from the linear regression analyses were used to determine TEAC values for the ABTS assays.

Measurement of 2,2'-azino-di-[3-ethylbenzthiazoline sulfonate (6)] (ABTS) radical scavenging activity. ABTS scavenging assays were performed according to previously published protocols with some modifications. A 10 mM stock solution of potassium persulfate was prepared in deionized water. A stock solution of ABTS was prepared by dissolving 7 mM ABTS and 2.45 mM potassium persulfate in deionized water. This solution was allowed to incubate at room temperature in the dark for 12-16 h to allow potassium persulfate to oxidize the ABTS. Following oxidation, the solution was a dark blue/green color. This solution was stable in the dark at room temperature for at least 48 h. This solution was diluted with 100 mM phosphate buffered saline, pH 7.2 so that the final absorbance was 0.70±0.02 at 734 nm. Stock solutions for all peptides and for Trolox were prepared in a range from 0.1 mM to 3.2 mM in 100 mM phosphate buffered saline, pH 7.2. To test the ability of Trolox and peptides to reduce the ABTS radical cation, samples were prepared with 990 μL of the diluted ABTS solution and 10 μL of each of the peptide or Trolox stock solutions. For every trial, one sample was prepared with 990 μL ABTS and 10 μL of buffer. The samples were allowed to incubate at room temperature in the dark for 10 min. The spectrophotometer was blanked with 1 mL of 100 mM phosphate buffered saline, pH 7.2 from 200-800 nm. Scans were taken for each of the samples and the change in absorbance at 734 nm was monitored. Every sample was run in triplicate and the results were averaged. The percentage of inhibition of ABTS oxidation was calculated using Equation 2.

$$ABTS \text{ scavenging } (\%) = \frac{A_{control} - A_{sample}}{A_{control}} \times 100 \quad \text{Eq. 2}$$

where $A_{control}$ is the absorbance of the control (ABTS and buffer only) and $A_{sample}$ is the absorbance at 734 nm of the test peptide/standard. A Trolox calibration curve was prepared with concentrations ranging from 1-32 μM (FIG. 14). Similar curves were prepared for each of the peptides (FIG. 14). These curves were used to calculate TEAC values for each of the peptides by calculating the ratio of peptide to Trolox to achieve the same percent reduction of ABTS.

Measurement of hydroxyl radical scavenging activity. Hydroxyl radical scavenging activity of peptides was measured with room temperature EPR spectroscopy according to known methods with some modifications. Hydroxyl radicals were generated by the iron-catalyzed Fenton Haber-Weiss reaction, and the generated hydroxyl radicals were reacted with the nitrone spin trap 5,5-dimethyl-1-pyrroline-N-oxide (DMPO). The resultant DMPO-OH adducts were detectable with EPR spectroscopy. The peptide (1 mM final concentration) was added to a solution containing: 24 mM DMPO, 0.8 mM $FeSO_4$, and 0.8 mM $H_2O_2$ in 100 mM potassium phosphate buffer, pH 7.4 in a final reaction volume of 250 μL. This solution was immediately transferred into a 50 μL quartz capillary tube. After 5 min, the EPR spectrum was recorded using a Bruker X-band EPR spectrometer operating at 9.42 GHz. The experimental conditions employed were as follows: magnetic field, 336.5±10 mT; power, 2 mW; modulation amplitude, 2.00 G; time constant, 327.68 ms, modulation frequency, 100 kHz; receiver gain, 30 dB sweep time, 60 s. Trials were performed in triplicate for each peptide. The double integral of the EPR spectra was obtained and used to determine the signal intensity for each sample. The hydroxyl radical scavenging ability was calculated using Equation 3, in which H and $H_0$ are relative peak height of radical signals with and without sample, respectively.

$$\text{Hydroxyl radical scavenging } (\%) = \frac{1 - H}{H_0} \times 100 \quad \text{Eq. 3}$$

Spectrophotometric determination of Cu (II) binding constants ($K_D$). The Cu(II) binding constants for carnosine and thioHcarnosine were quantified by titrating each peptide with Cu(II) and monitoring changes in the absorbance spectra. To detect formation of the Cu(II) complex, 10 mM carnosine in 50 mM MOPS buffer, pH 7.4 was titrated with $CuCl_2$ at concentrations ranging from 1-25 mM, whereas 100 μM thioHcarnosine in 50 mM MOPS buffer, pH 7.4 was titrated with $CuCl_2$ at concentrations ranging from 5-250 μM. The thioHcarnosine/Cu(II) solution was allowed to incubate at room temperature for 40 min before absorbance spectra were recorded to ensure complete formation of the Cu(II) complex. Both peptides had a unique wavelength of maximum absorbance for the Cu(II) complex: thioHcarnosine at 260 nm and carnosine at 630 nm. The $K_A$ values were calculated by fitting the resulting titration data to the appropriate equation describing the association constant. The $K_D$ values were calculated from the reciprocal of the $K_A$ value for each peptide.

Low temperature EPR studies. The ability of each peptide to bind Cu(II) was determined by low temperature (95 K) EPR spectroscopy using the methods known in the art with some modifications. Samples of 200 μM and 400 μM peptide were incubated for 10 min at room temperature with 200 μM $CuCl_2$ in 100 mM potassium phosphate, pH 7.4. Following incubation, aliquots of each sample were transferred into 4 mm inner diameter quartz EPR tubes (Wilmad-LabGlass). The samples were frozen in liquid nitrogen and stored in liquid nitrogen prior to use. Control samples were prepared with only buffer and with 200 μM $CuCl_2$ in potassium phosphate buffer. Low temperature EPR spectra were gathered with a Bruker EPR spectrometer operating at 9.42 GHz with the following parameters: scan range, 6000 G; field set, 3200 G; time constant, 164 ms; scan time, 60 s; modulation amplitude, 7.000 G; modulation frequency, 100 kHz; receiver gain, 30 dB; microwave power, 20 mW; and number of scans, 5.

Results and Discussion

Past use of 2-thioHis in peptides. As mentioned in the above, 2-thioHis has only been incorporated into a peptide one time in the entire history of peptide science. While lack of commercial availability is certainly one cause for its dearth of use in peptides, it can be readily synthesized from histidine (His) and cysteine (Cys) via a labile His-bromolactone intermediate on a gram scale. The problem of protection/deprotection of the thione has likely created a barrier to entry for many peptide chemists such that 2-thioHis has not been incorporated into a peptide since their initial report (31 years).

Figure 3:
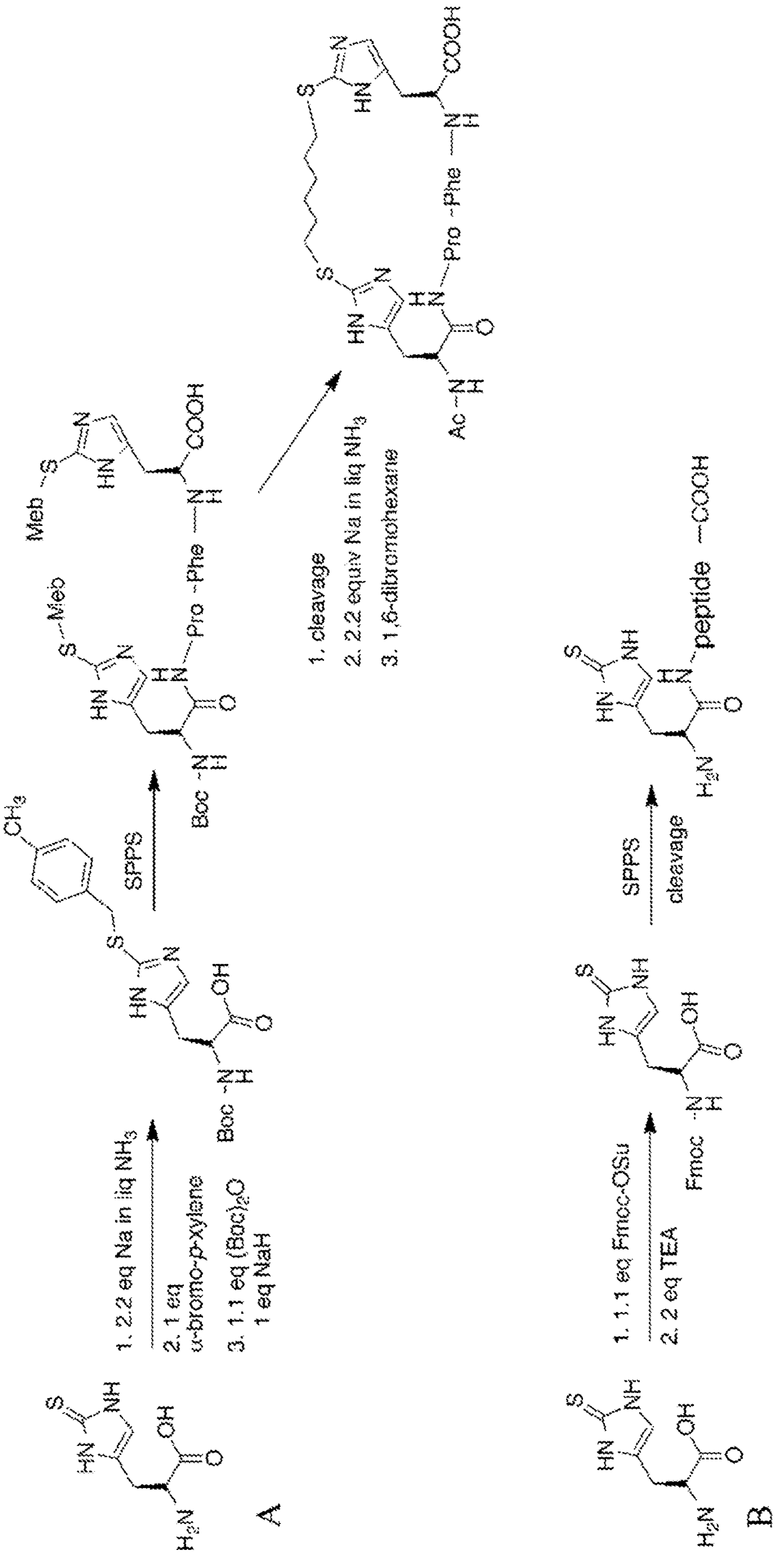
FIG. 3 shows inserting 2-thioHis into a peptide. A) Method known in the art to protect 2-thioHis before insertion into a peptide, followed by deprotection in the presence of linker. B) The method disclosed herein, which is a simplified method eliminates protection of 2-thioHis prior to insertion into a peptide.
Figure 4:
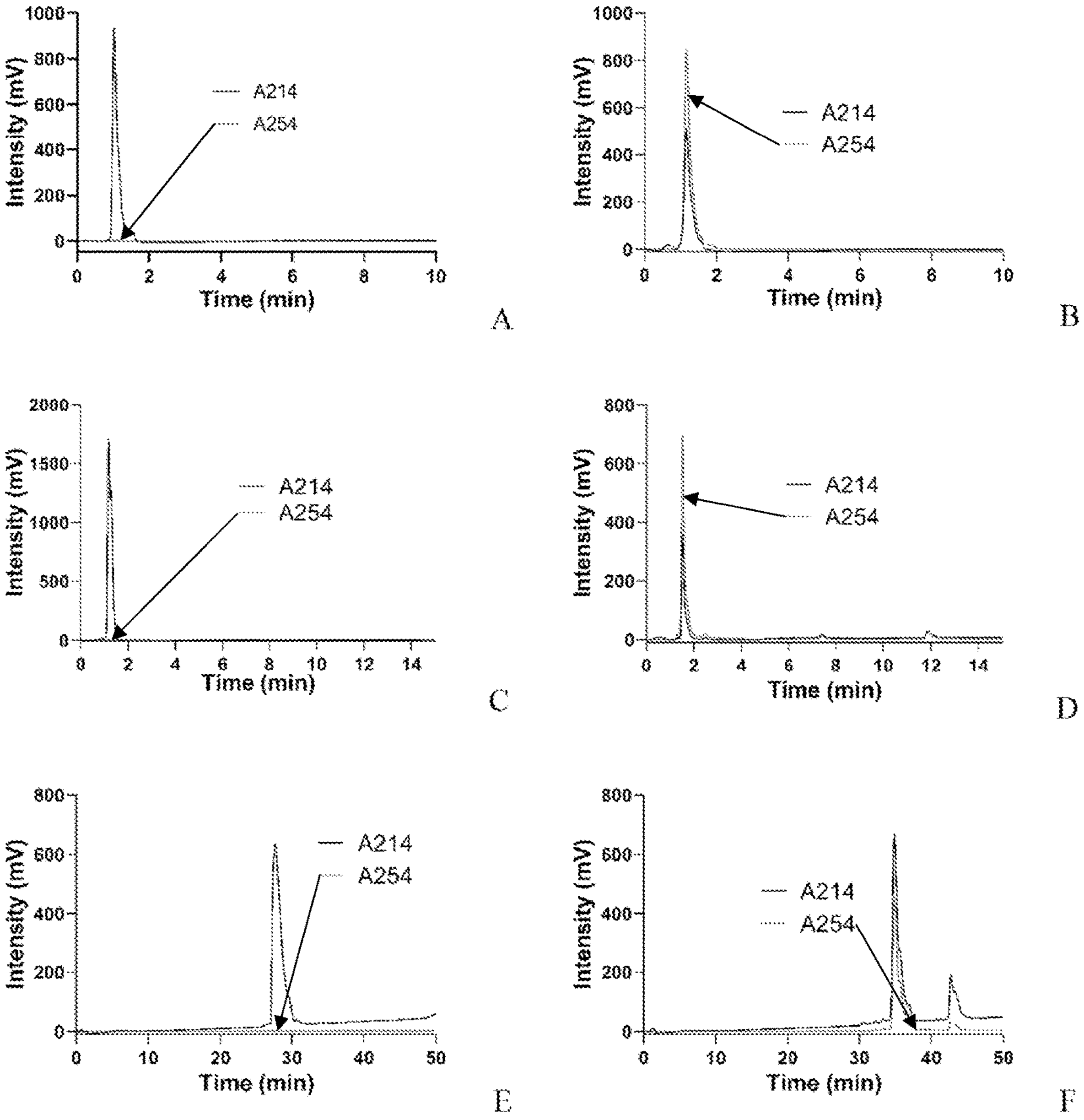
FIG. 4 shows analytical HPLC analysis of His- and thioHis-containing peptides in this study. A) GHK. B) GthioHK. C) carnosine. D) thioHcarnosine. E) HGPLGPL. F) thioHGPLGPL.

In order to achieve protection of the thione, others have used harsh conditions consisting of sodium dissolved in liquid ammonia followed by addition of α-bromo-p-xylene to install the Meb group on the sulfur. The Boc-2-thioHis (Meb) derivative was then incorporated into a peptide using Merrifield SPPS. After synthesis of the peptide was complete, deprotection was achieved using an excess of monohalogenated alkanes such as bromomethane or excess bishalogenated alkanes in sodium/liquid ammonia to yield various monoalkylated and bisalkylated products (FIG. 3). Of note, they were able to create a unique disulfide mimic by connecting two 2-thioHis residues with an alkyl linker by addition of 1,6-dibromohexane in the sodium/liquid ammonia reaction.

The present disclosure describes incorporation of 2-thioHis into a peptide without protecting the thione due to the reported low reactivity of EGT with DTNB, a highly reactive disulfide. If 2-thioHis could be used without a protecting group, this would remove a large barrier to using 2-thioHis in peptide synthesis.

Synthesis and analysis of 2-thioHis-containing peptides. These results show successful insertion of 2-thioHis into the three target peptides in place of His using standard Fmoc SPPS techniques with carbodiimide-mediated coupling. The three peptides chosen place 2-thioHis as the first amino acid coupled (thioHcarnosine), the middle amino acid coupled (GthioHK), or the last amino acid coupled (thioHGPLGPL). The yield of each peptide after lyophilization was 90% or greater.

Figure 15:
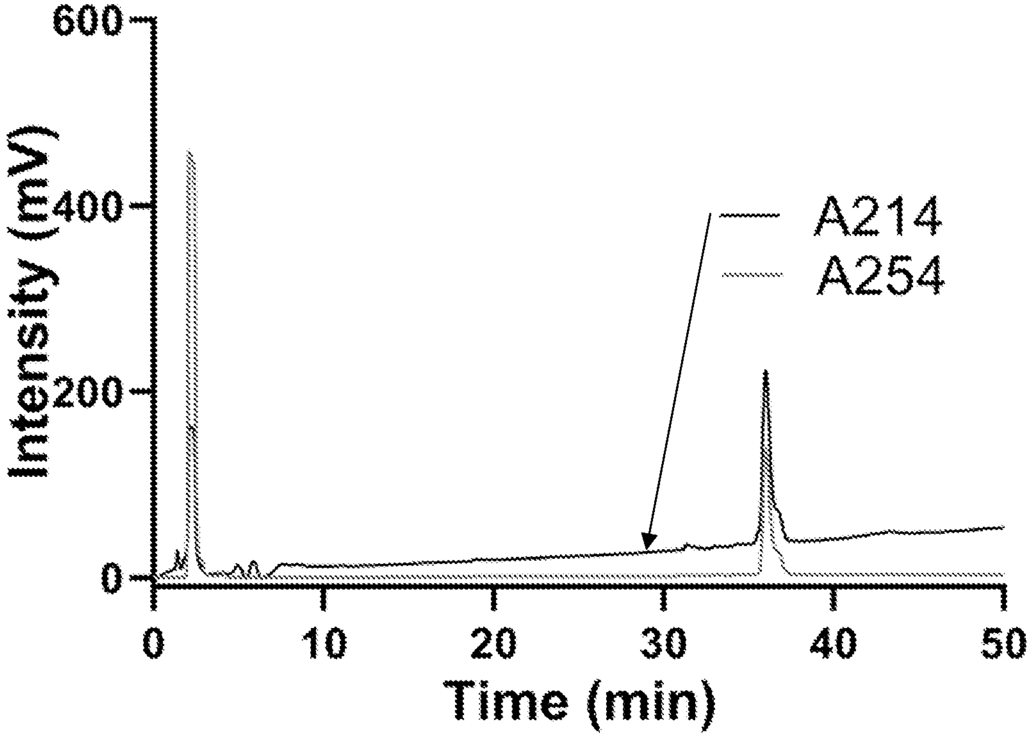
FIG. 15 shows HPLC trace of thioHGPLGPL reduced by incubation with 10 mM Asc, pH 4.5. HPLC trace of thioHGPLGPL after incubation with 10 mM ascorbate, pH 4.5 for 1 h. Notice the peak at 43 mins disappears, suggesting that this peak is the peptide disulfide.
Figure 16:
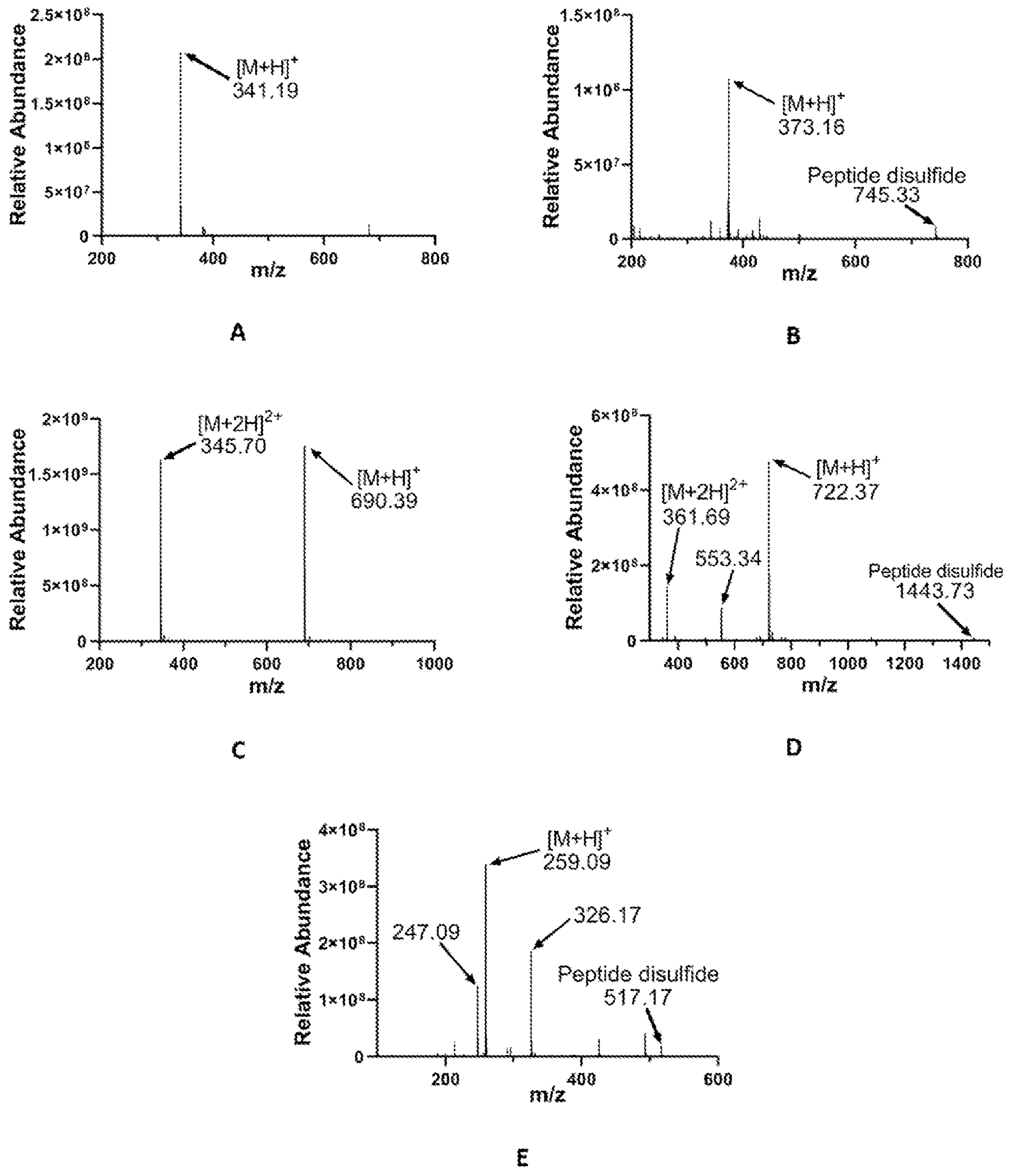
FIG. 16 shows mass spectra of all peptides synthesized. A) Mass spectrum of GHK peptide. B) Mass spectrum of GthioHK peptide. C) Mass spectrum of HGPLGPL peptide. D) Mass spectrum of thioHGPLGPL peptide with an unknown contaminant at 553.34 m/z. E) Mass spectrum of thioHcarnosine peptide, 247.09 m/z and 326.17 m/z are unknown contaminants.

HPLC analysis of the 2-thioHis-containing peptides shows that the purity of the GthioHK and thioHcarnosine peptides were nearly identical to their His-containing counterparts (FIG. 4A-4D). It was noted that 2-thioHis-containing peptides are readily identified in the analytical HPLC due to their strong absorbance at 254 nm. The imidazothione of 2-thioHis has a $\lambda_{max}$ at 257 nm with an extinction coefficient 14,000 $M^{-1}$ $cm^{-1}$. In the case of peptide thioHGPLGPL, an unidentified peak that eluted very late in the gradient was observed. The main peak corresponding to thioHGPLGPL is clearly identified in the chromatogram due to the very strong absorbance at 254 nm (FIG. 4F). The unidentified peak has a much less intense absorbance at 254 nm. It is possible that this unidentified peak is a significant impurity due to a side-reaction or incomplete coupling. However, another possibility is that this peak is the disulfide form of the peptide. A disulfide can form between two 2-thioHis residues as was observed during the synthesis of Fmoc-2-thioHis as indicated herein. This peptide was synthesized several times and this peak was always present. To investigate the possibility that this was the disulfide, the sample was incubated with 1 mM Asc at pH 4.5 for 1 h and then injected the reaction onto the column. The result showed that the unidentified peak disappeared (FIG. 15). This is strong evidence that this peptide formed a disulfide between two monomers following precipitation into ether and dissolution into water prior to lyophilization. In fact, the MS analysis of each peptide shows evidence for disulfide formation. The MS analysis of each peptide in FIG. 4 is given in FIG. 16. The disulfide bond between two 2-thioHis residues must be very weak since Asc was able to reduce it.

Figure 5:
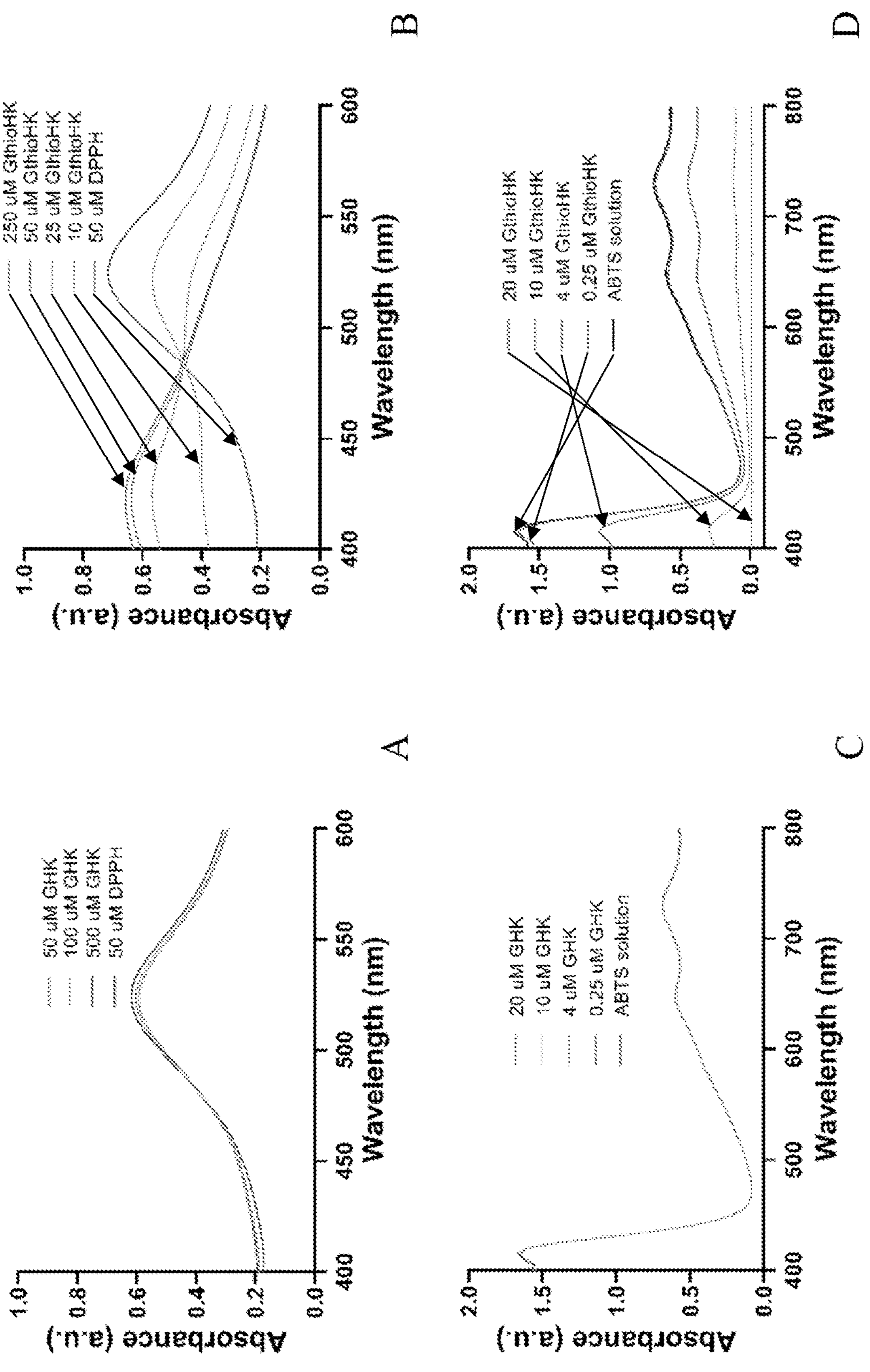
FIG. 5 shows radical scavenging ability of peptides against DPPH and ABTS. A) Absorbance spectrum for 50 μM DPPH with different concentrations of GHK peptide. B) Absorbance spectrum for 50 μM DPPH with different concentrations of GthioHK peptide. C) Absorbance spectrum for ABTS solution with different concentrations of GHK peptide. D) Absorbance spectrum for ABTS solution with different concentrations of GthioHK peptide.
Figure 17:
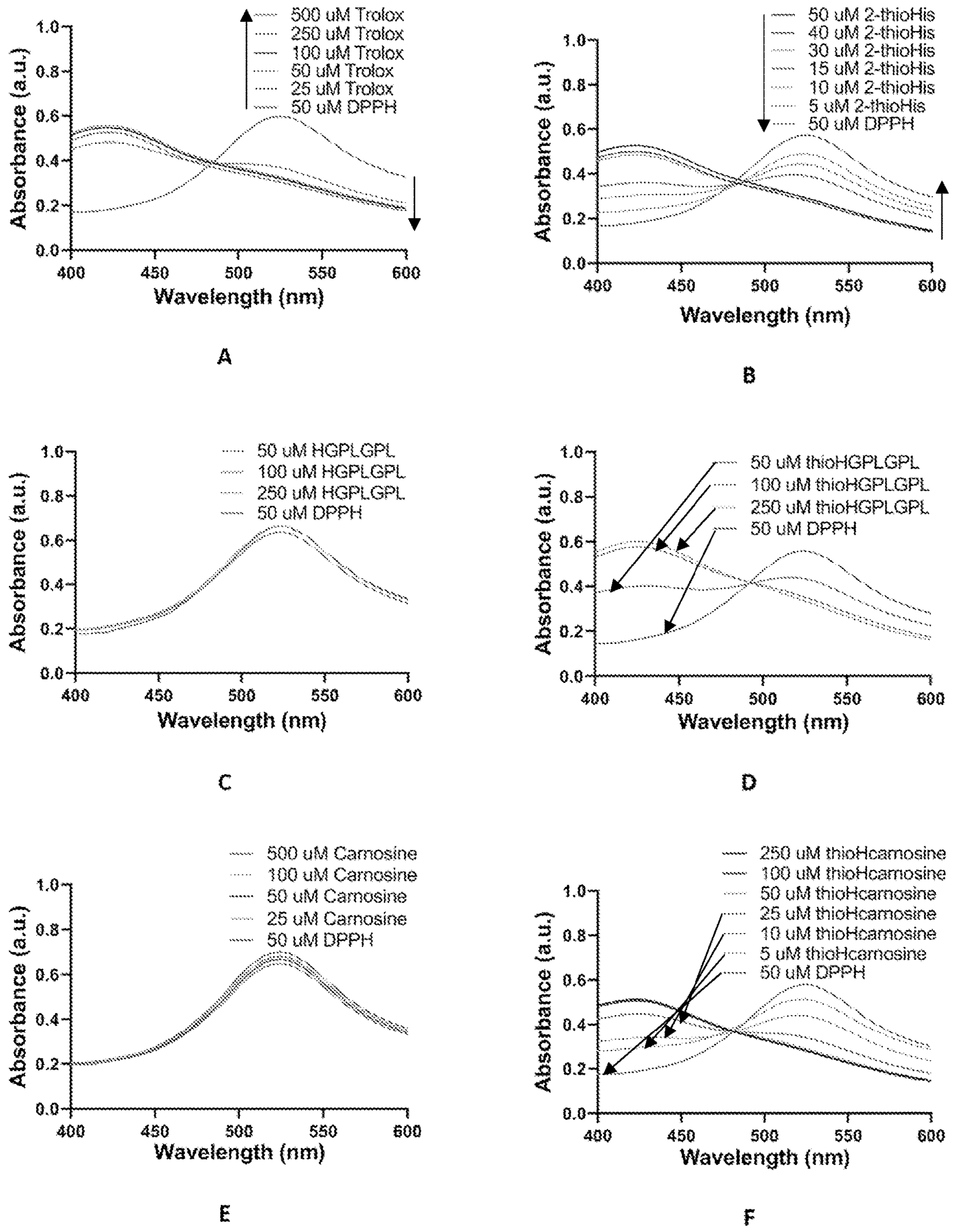
FIG. 17 shows UV/Vis spectra showing DPPH radical scavenging activity for all peptides and compounds tested. A) Trolox and DPPH assay UV-Vis absorbance spectra. B)

Antioxidant activity of 2-thioHis-containing peptides. The His- and 2-thioHis containing peptides, as well as 2-thioHis, were tested for their ability to scavenge DPPH and ABTS. Trolox, a water-soluble vitamin E analogue, was used as a standard for the ABTS and DPPH assays. The reduction of DPPH and ABTS was determined by monitoring the decrease in absorbance at 517 nm and 734 nm, respectively, after the addition of peptide or standard. The His-containing peptides all showed little or no ability to scavenge DPPH or ABTS radicals at the concentration of peptides chosen here. It is noted that carnosine and HGPLGPL (SEQ ID NO:1) have been reported to scavenge the DPPH radical, but at higher concentrations than we tested. Peptide GHK was the strongest antioxidant peptide tested of the His-containing peptides and caused only a slight decrease in the DPPH absorbance peak at 517 nm and no decrease in the ABTS absorbance peak at 734 nm (FIG. 5). In contrast to the His-containing peptides, all of the 2-thioHis-containing peptides showed strong radical scavenging activity with both DPPH and ABTS radicals. Peptide GthioHK was the strongest antioxidant peptide tested overall with the ability to completely reduce the DPPH and ABTS radicals (FIG. 5). The same absorbance spectra for the other peptides in this study are given in FIGS. 17 and 18.

Figure 6:
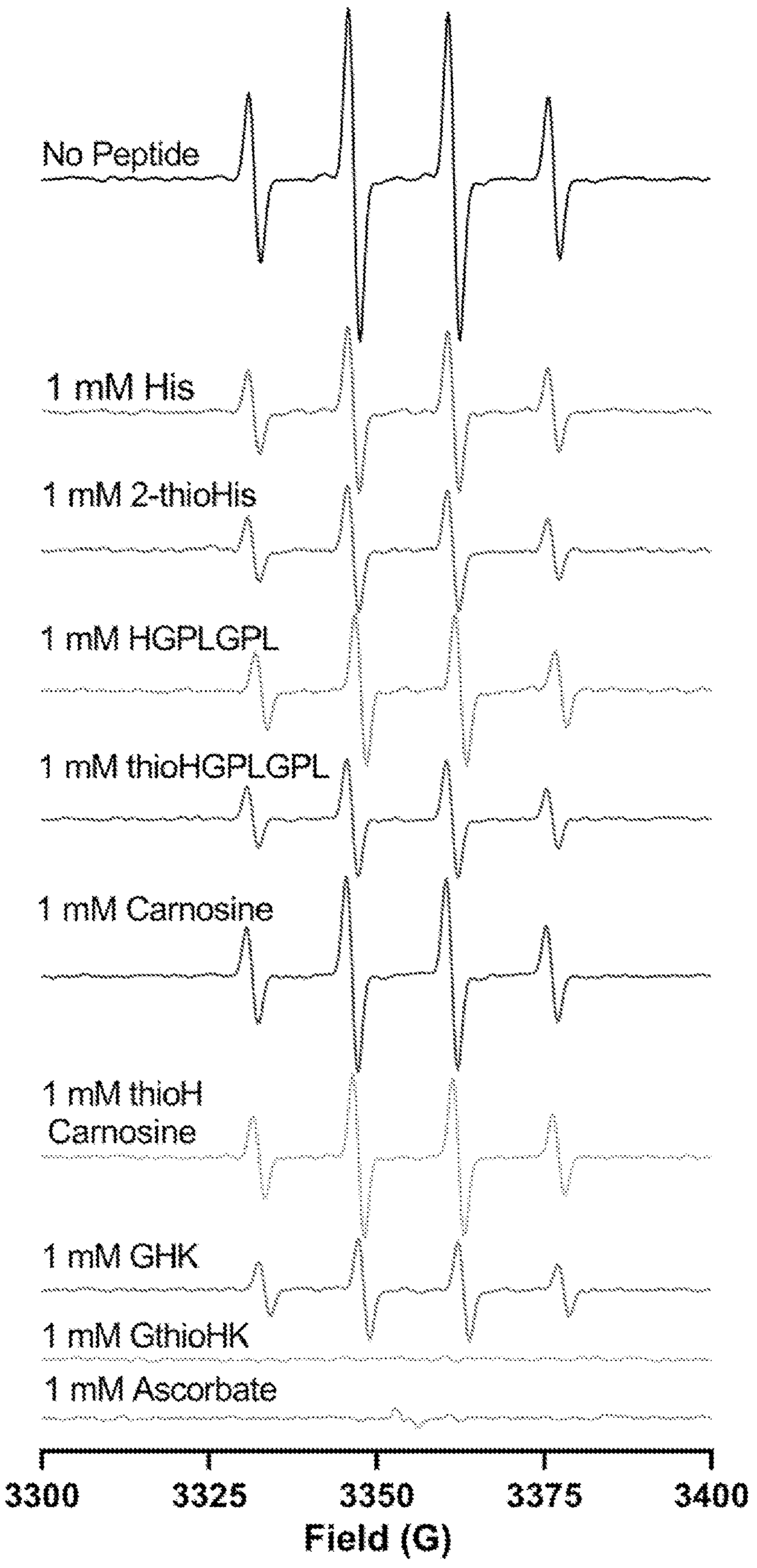
FIG. 6 shows hydroxyl radical scavenging activity of peptides measured by EPR. The hydroxyl radicals were trapped with DMPO prior to obtaining spectra.

Next, the His- and 2-thioHis containing peptides, as well as 2-thioHis, were tested for their ability to scavenge ·OH. Asc was used as a standard for ·OH scavenging activity, with 1 mM Asc completely reducing the ·OH. The reduction of ·OH was measured using EPR spectroscopy. The Fenton Haber-Weiss reaction was used to produce ·OH in the presence of peptide and the spin-trapping reagent DMPO. The radical scavenging activity (RSA) was calculated by measuring the decrease in peak height upon addition of 1 mM peptide (final concentration) compared to the control with no peptide. All RSA values represent the average of three or more trials. Each of the peptides tested showed ability to scavenge ·OH, although the 2-thioHis-containing peptides showed improved activity over their His-containing counterparts. GthioHK had the highest RSA of all compounds tested. (FIG. 6, Table 1).

In comparing the ·OH scavenging ability of His with 2-thioHis, an increase of 7.5% (Table 1) was observed. A similar increasing in ·OH scavenging ability when substituting 2-thioHis for His in various peptides was expected. However, it was found that this substitution produced a synergistic effect for all of the peptides studied here, with the increase in ·OH scavenging ability ranging from a 12% to 13% increase for peptides thioHGPLGPL and thioHcarnosine, respectively, to a dramatic 31.6% increase for GthioHK (Table 1). It is interesting to note that in the case of thioHGPLGPL (SEQ ID NO:1, where His is replaced with 2-thioHis), the ·OH scavenging ability is equivalent to 2-thioHis itself, while for thioHcarnosine the ·OH scavenging ability is less than 2-thioHis. Carnosine itself was not a good ·OH scavenger in comparison to the other peptides tested. Substitution of His with 2-thioHis in peptide GHK produced the most dramatic and interesting result as is clearly evidenced by the EPR spectra shown in FIG. 6. The GthioHK peptide showed a similar RSA as Asc, with 1 mM GthioHK nearly completely abolishing the signal. Clearly, the 2-thioHis residue, in the context of the amino acid sequence of the peptide, produces an antioxidant that is much better than expected in comparison to the difference between the ability of His and 2-thioHis to scavenge ·OH. These data demonstrate that GHK itself is a good antioxidant, which agrees with other studies. The naturally occurring matrikine peptide GHK and its Cu(II) complex are commonly used in skin care products and cosmeceuticals. The GHK tripeptide has well-studied wound healing and anti-aging properties stemming in part from its ability to block the formation of reactive oxygen and carbonyl species as well as its ability to readily chelate redox active metals such as Cu(II) and Fe(II). Studies of the antioxidant capabilities of GHK have demonstrated its strong ability to scavenge ·OH in vitro suggesting it may play a role in managing oxidative stress in cells. The GthioHK analogue could also be potentially used as a therapeutic or in cosmetics due to its enhanced antioxidant properties.

TABLE 1

Antioxidant capacity of His- and 2-thioHis-containing peptides compared to Trolox or Ascorbate and 2-thioHis.

| Analyte or Peptide | ABTS radical TEAC | DPPH Radical TEAC | Hydroxyl Radical RSA[a] (%) |
|---|---|---|---|
| Trolox | 1.00 | 1.00 | NA[a] |
| Asc | NA[b] | NA[b] | 100 |
| His | NA[b] | NA[b] | 48.5 ± 7.3 |
| 2-thioHis | 1.50 ± 0.03 | 1.00 ± 0.02 | 56.0 ± 2.1 |
| HGPLGPL (SEQ ID NO: 1) | ND[c] | ND[c] | 46.8 ± 1.3 |
| thioHGPLGPL (SEQ ID NO: 1, where His is replaced with 2-thioHis) | 2.14 ± 0.02 | 0.95 ± 0.01 | 59.7 ± 3.0 |
| GHK | ND[c] | ND[c] | 65.4 ± 0.008 |
| GthioHK | 2.61 ± 0.01 | 0.95 ± 0.02 | 97.0 ± 0.3 |
| Carnosine | ND[c] | ND[c] | 31.4 ± 4.2 |
| thioHCarnosine | 2.25 ± 0.05 | 0.80 ± 0.01 | 43.5 ± 1.1 |

[a]All analytes were tested at a concentration of 1 mM.
[b]Not applicable since it was not used in the assay.
[c]The activity was too low to be determined, these peptides have TEAC values close to zero and are not comparable to Trolox.

Summary of antioxidant activities of 2-thioHis-containing peptides. The antioxidant capacities of all peptides tested were compared by calculating TEAC values for both the ABTS and DPPH assays (Table 1). All TEAC values represent the average from three or more trials. The curves used to determine TEAC values for 2-thioHis peptides are shown in FIGS. 13 and 14 of the Supporting Information. The His-containing peptides all had TEAC values of approximately 0 and showed no ability to scavenge the ABTS radical at the concentrations tested (Table 1). The 2-thioHis-containing peptides possessed high ABTS radical scavenging activity, with GthioHK having a slightly higher TEAC value than the other 2-thioHis peptides. All three 2-thioHis-containing peptides were stronger scavengers of the ABTS radical compared to both Trolox and 2-thioHis on its own (Table 1). 2-thioHis had the same ability as Trolox to scavenge the DPPH. The His-containing peptides showed no significant ability to scavenge the DPPH radical even at 10:1 peptide: DPPH (Table 1 and FIG. 17). In contrast, the 2-thioHis-containing peptides showed significant ability to scavenge the DPPH radical, however, they were less efficient than Trolox and took longer to react with the radical likely due to steric hindrance (Table 1). Although the kinetics of the reaction was not studied herein specifically, an immediate color change of the DPPH solution upon addition of Trolox (change from purple to orange color) was noticed, while the 2-thioHis-containing peptides took several minutes to achieve the same color change. The ability of the 2-thioHis-containing peptides to scavenge the DPPH radical and ABTS radical indicates that the presence of 2-thioHis imparts strong antioxidant activity to these peptides. In comparison, the His-containing peptides had very weak antioxidant activity in the same assays.

Figure 7:
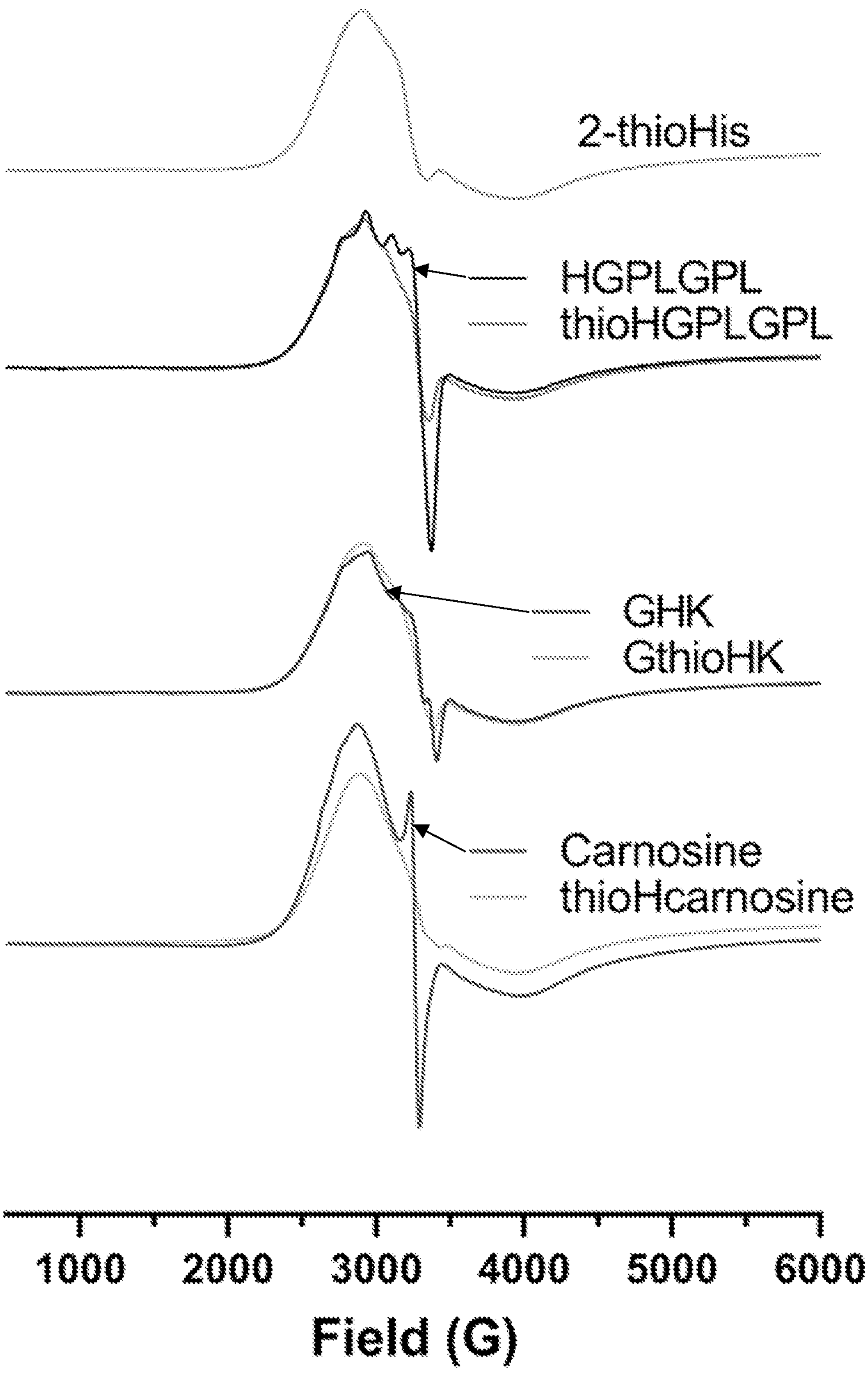
FIG. 7 shows low temperature EPR spectra of peptide-Cu(II) complexes in potassium phosphate buffer, pH 7.4. All peptides and 2-thioHis are at a concentration of 400 μM with 200 μM $CuCl_2$.

Copper binding ability of 2-thioHis-containing peptides. Next, the stoichiometry and affinity of copper binding of the 2-thioHis-containing peptides in comparison to the His-containing peptides was investigated. The ability of the test peptides to chelate Cu(II) was determined with low temperature (95 K) EPR spectroscopy. The EPR experiments showed that the 2-thioHis-containing peptides could all bind Cu(II) as evidenced by the disappearance of the Cu(II) signature in the EPR spectra and the change in peak shape and position (FIG. 7). Comparing the EPR spectra of the 2-thioHis-containing peptides to that of 2-thioHis indicates that the 2-thioHis containing peptides bind Cu(II) in a similar configuration as 2-thioHis (FIG. 7). The 2-thioHis-Cu(II) complex peak is almost identical to the peaks for the three 2-thioHis containing peptides indicating that these peptides are binding Cu(II) through the sulfur (FIG. 7). In contrast, all of the His-containing peptides have unique EPR spectra compared to each other, which indicates differences in Cu(II) binding geometry between the three of them or differences in Cu(II) binding affinity. (FIG. 7).

Figure 8:
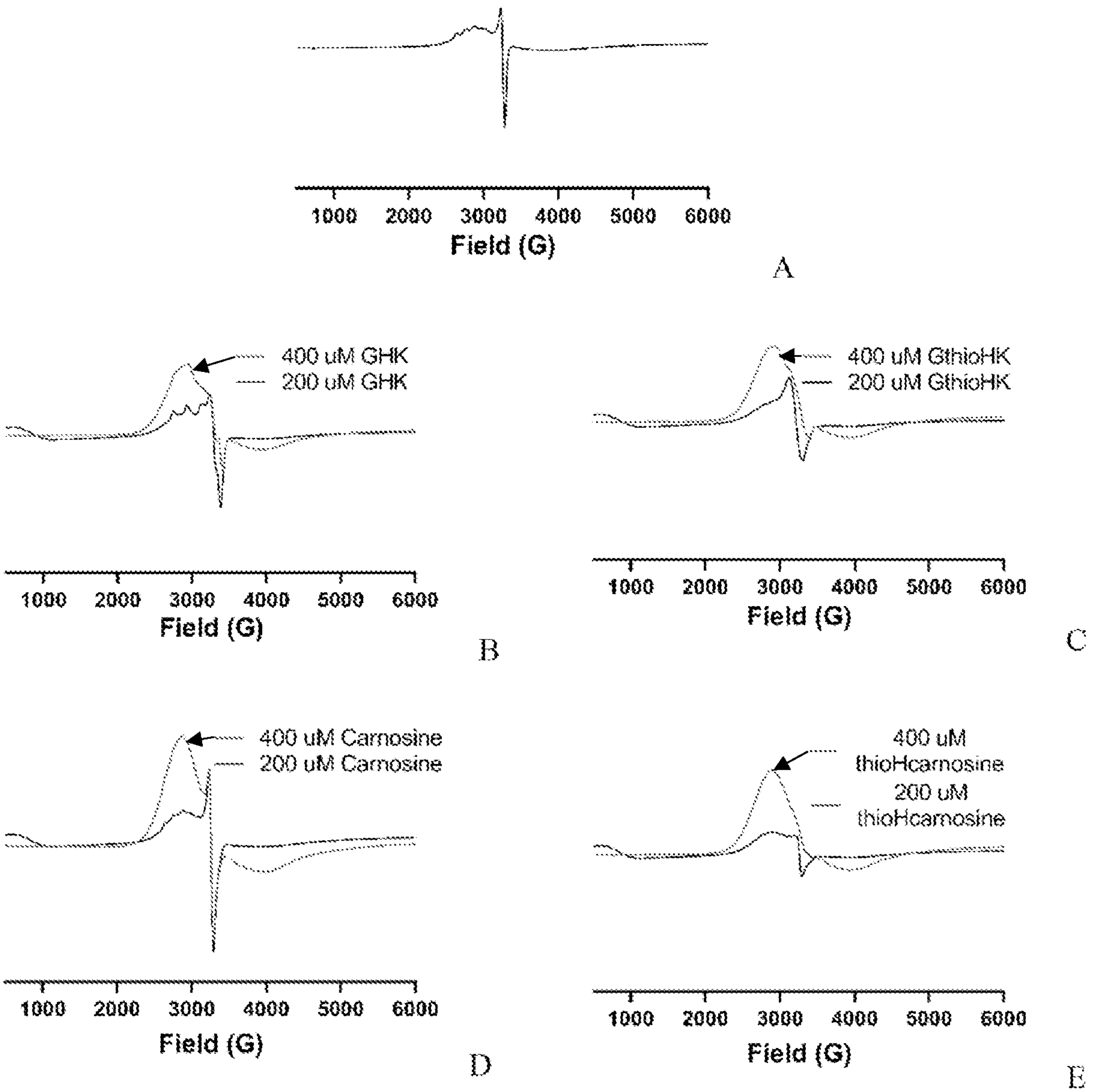
FIG. 8 shows low temperature EPR spectra of peptide-Cu(II) complexes in potassium phosphate buffer, pH 7.4. A) 200 μM $CuCl_2$, B) GHK with 200 μM $CuCl_2$, C) GthioHK with 200 μM $CuCl_2$, D) carnosine with 200 μM $CuCl_2$, E) thioHcarnosine with 200 μM $CuCl_2$.

In addition to Cu(II) binding ability, the EPR data in FIG. 8 offers some insight into the equilibrium dissociation constants ($K_D$) and binding stoichiometry for some of the peptides. For peptide GHK, the $K_D$ for Cu(II) has previously been determined to be $7.0\times10^{-14}$ M using isothermal titration calorimetry with competitive chelators (such as glycine) in different buffer systems. Because GHK has a very high affinity for Cu(II), it can be concluded that in the conditions used for EPR, all of the Cu(II) in solution would be bound to GHK. Based on this information, it was concluded from the EPR spectra that GHK binds to Cu(II) in a 2:1 ratio because at 1:1 GHK:Cu(II) the Cu(II) trace is still visible in the EPR spectrum, but with 2:1 GHK:Cu(II) the Cu(II) trace is almost completely gone (FIG. 8). The EPR spectra for GthioHK shows a similar trend indicating that GthioHK, like 2-thioHis and GHK, likely also binds Cu(II) in a 2:1 ratio (FIG. 8).

However, the affinity for Cu(II) and binding stoichiometry appears to be significantly different for carnosine in comparison to thioHcarnosine upon comparison of their EPR spectra (FIG. 8). The $K_A$ value reported in the literature for carnosine is 1.1 M, which indicates a weak affinity for Cu(II). Carnosine has been reported to bind Cu(II) in a 1:1 ratio which is confirmed in the EPR spectra as the Cu(II) trace is still highly visible at both 1:1 and 2:1 peptide:Cu(II) (FIG. 8). While quantitative determinations of $K_A$ for thioHcarnosine from the EPR spectra cannot be made, it can reasonably conclude that it has a higher affinity for Cu(II) than carnosine due to the lack of a strong Cu(II) signal at 1:1 thioHcarnosine:Cu(II) (FIG. 8). In addition, it can be concluded that unlike carnosine, thioHcarnosine binds Cu(II) with a 2:1 stoichiometry as indicated by the change in the EPR signal as the peptide concentration is increased from 200 μM to 400 μM while keeping the Cu(II) concentration constant at 200 μM (FIG. 8).

Based on the comparison of EPR spectra of the His and 2-thioHis-containing peptides, it was also concluded that substitution of 2-thioHis for His in peptides can change the Cu(II) binding geometry, binding affinity, and binding stoichiometry. The comparison of the 2-thioHis-containing peptides to their His counterparts and free 2-thioHis indicates that these peptides are binding Cu(II) through the sulfur with a geometry similar to 2-thioHis. Using known $K_A$ values for GHK and carnosine, it can also be concluded that insertion of 2-thioHis in place of His resulted in a 2:1 peptide: Cu(II) binding geometry, and in the case of thioHcarnosine, also increased the Cu(II) binding affinity.

Figure 9:
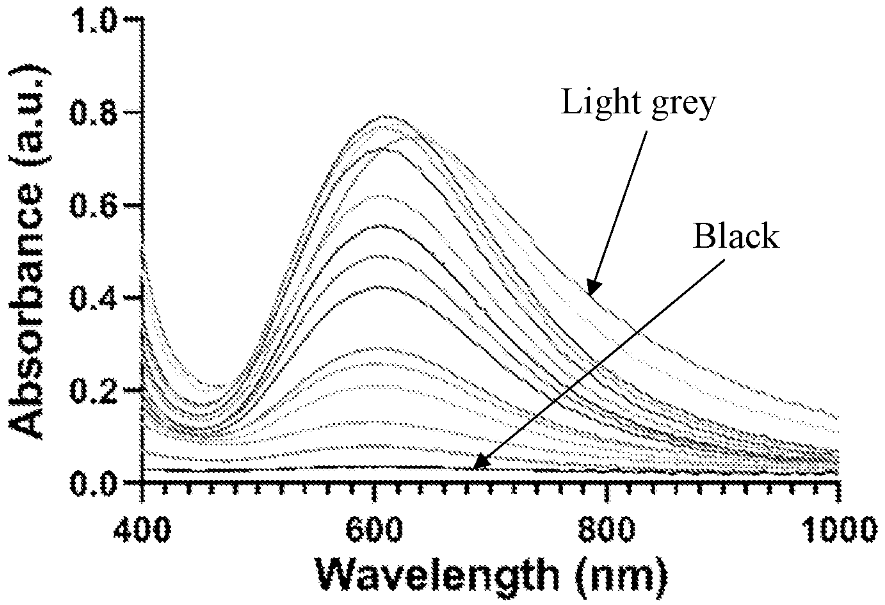
Figure 9:
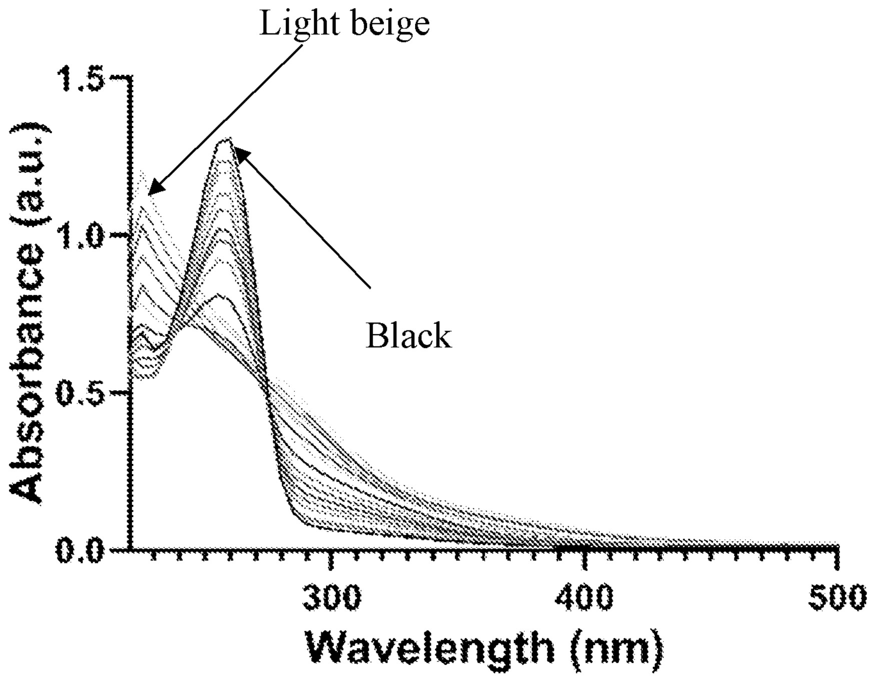
Figure 10:
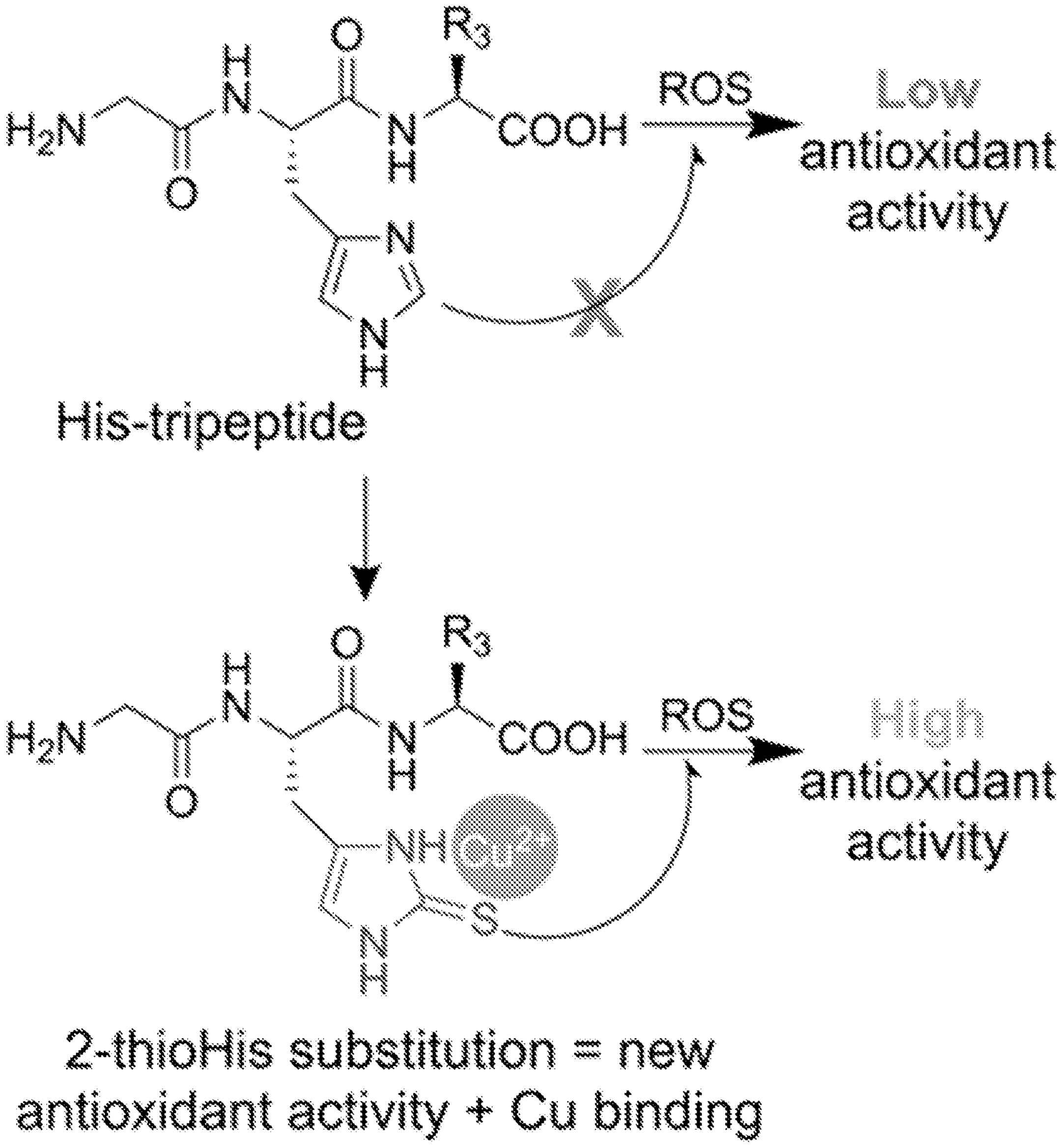
FIG. 10 shows 2-thiohistidine is an analogue of the antioxidant vitamin-like compound ergothioneine (EGT). Unlike EGT, 2-thiohistidine can be substituted for histidine in a peptide. This substitution gives the peptide novel antioxidant and metal binding abilities.
Figure 11:
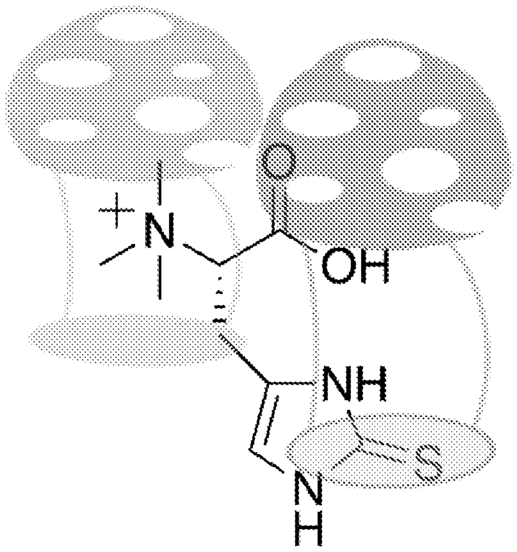
FIG. 11 shows 2-thiohistidine is an analogue of the antioxidant vitamin-like compound ergothioneine (EGT). Unlike EGT, 2-thiohistidine can be substituted for histidine in a peptide. This substitution gives the peptide novel antioxidant and metal binding abilities.
Figure 11:
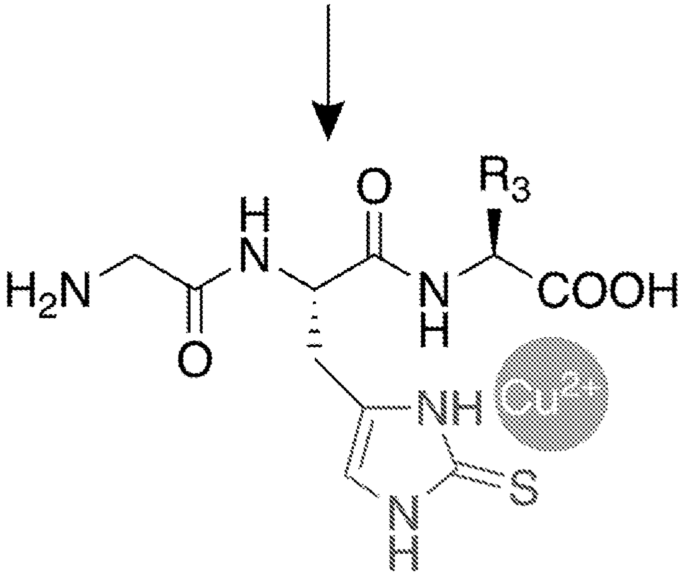

Quantification of $K_D$ for Cu(II) was attempted for carnosine and thioHcarnosine via titration of Cu(II) using UV-Vis spectroscopy. As known in the art, carnosine forms a blue complex when binding Cu(II) which can be detected at 630 nm. This blue complex was detected upon addition of Cu(II) to carnosine as is shown by the plot of absorbance versus wavelength at various Cu(II) concentrations as shown in FIG. 9A. A plot of the change in absorbance at 630 nm vs. Cu(II) concentration was made (FIG. 19). The resulting curve was fit to the appropriate equation for a 1:1 association constant. This yields an association constant ($K_A$) of 0.228 M ($K_D$=4.39 M). This compares to a reported value of 1.1 M. The measurement was made in MOPS buffer at pH 7.4, while the literature value was determined in pure water.

The same analysis for thioHcarnosine was performed, as shown by the absorbance scan shown in FIG. 9B. However, the same analysis was unable to be done because of the strong absorbance of the 2-thioHis residue at 255 nm, which limited the concentration of peptide that could be analyzed by UV-Vis spectroscopy. Thus the experiment with thioHcarnosine was performed on a different scale from carnosine, rendering comparison impossible using this method. However, the EPR data in FIG. 8 suggests that thioHcarnosine binds Cu(II) more tightly than carnosine, but this parameter was not quantified.

Conclusions

The decision to leave the thione of 2-thioHis unprotected during SPPS while seemingly unconventional, proved to be sound and enabled the facile synthesis of multiple biologically relevant peptides. The present disclosure has shown that the substitution of 2-thioHis for His in bioactive peptides greatly enhances their existing antioxidant properties, equal to that of 2-thioHis, or in some cases much more. An example of this greater enhancement is substitution of 2-thioHis for His in the matrikine GHK-tripeptide, which very strongly quenched both the ABTS and hydroxyl radicals. Substitution of His with 2-thioHis also confers the ability to bind $Cu^{2+}$ ions to the peptide.

Abbreviations

ABTS, 2,2'-azino-di-[3-ethylbenzthiazoline sulfonate; Asc, ascorbate; βA, β-alanine; ABTS, 2,2'-azino-di-[3-ethylbenzthiazoline sulfonate (6)]; H-βAH-OH or βAH, carnosine; Cu(II), copper (II); Cys, cysteine; DCM, dichloromethane; DIC, diisopropylcarbodiimide; DPPH, 2,2-diphenyl-1-picrylhydrazyl; DMF, dimethylformamide; DMPO, 5,5-dimethyl-1-pyrroline-N-oxide; DTNB, 5,5'-dithiobis(2-nitrobenzoic acid); EGT, Ergothioneine; EPR, electron paramagnetic resonance; $K_A$, equilibrium association constant; $K_D$, equilibrium dissociation constant; EtCA, ethyl (hydroxyimino)cyanoacetate; Fmoc, fluorenylmethoxycarbonyl; Fmoc-OSu, Fmoc N-hydroxysuccinimide ester; HATU, 1-[Bis(dimethylamino)methylene]-1H-1,2,3-triazolo[4,5-b]pyridinium 3-oxide hexafluorophosphate; His, histidine, HPLC, High-pressure liquid chromatography; ·OH, hydroxyl radical; MS, mass spectrometry or mass spectrometric; Meb, 4-methylbenzyl; NMM, N-methylmorpholine; RSA, radical scavenging activity; ROS, reactive oxygen species; SPPS, solid-phase peptide synthesis; TEA, triethylamine; TFA, trifluoroacetic acid; 2-thioHis, 2-thio-Histidine; TIS, triisopropylsilane; TLC, thin-layer chromatography; Trolox, 6-hydroxy-2,5,7,8-tetramethylchroman-2-carboxylic acid; TEAC, Trolox equivalent antioxidant capacity; UV-Vis, ultraviolet-visible.

Although the present disclosure has been described with respect to one or more particular embodiments and/or examples, it will be understood that other embodiments and/or examples of the present disclosure may be made without departing from the scope of the present disclosure.

The invention claimed is:

1. A method for making a modified peptide comprising: contacting a reaction mixture comprising a solvent,

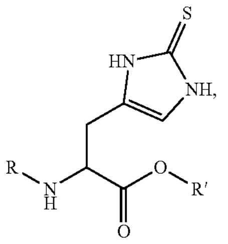

optionally, a carbodiimide, and, optionally, a base, wherein R is an amine protecting group and R' is an H or group formed from a carbodiimide, with:

i) an amine group of a first amino acid covalently attached to a resin, peptide covalently attached to a resin, a peptidomimetic covalently attached to a resin, or resin, or ii) an alcohol of a first amino acid derivative attached to a resin, peptidomimetic attached to a resin, or resin, or iii) a carbocation of a resin;

optionally, removing the amine protecting group of the amine group of

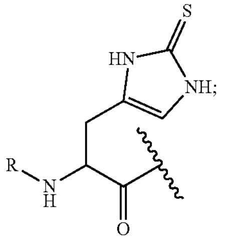

optionally, coupling a second amino acid, wherein the second amino acid is N-protected, to the unprotected amine;

optionally, cleaving the N-protecting group of the second amino acid, optionally, repeating the coupling amino acid step and subsequent cleaving N-protecting group step; and cleaving the modified peptide from the resin, wherein the modified peptide is formed.

2. The method according to claim 1, further comprising functionalizing the N-terminus of the modified peptide on resin with a capping group and/or a linking group prior to cleavage.

3. The method according to claim 2, wherein the capping group is an acetyl group, a palmitoyl group, or an ascorbic acid group.

4. The method according to claim 2, wherein the linking group is a succinyl group, polyethylene glycol group, or a combination thereof.

5. The method according to claim 1, wherein the resin is a Rink resin, a Wang resin, a trityl resin, or a chlorotrityl resin.

6. The method according to claim 1, further comprising purifying the modified peptide.

7. The method according to claim 1, wherein the group formed from a carbodiimide is formed from diisopropylcarbodiimide (DIC), 1-hydroxybenzotriazole (HOBt), 1-hydroxy-7-azabenzotriazole (HOAt), 2-(1H-benzotriazol-1-yl)-1,1,3,3-tetramethyluronium hexafluorophosphate (HBTU), or 1-[Bis(dimethylamino)methylene]-1H-1,2,3-triazolo[4,5-b]pyridinium 3-oxide hexafluorophosphate (HATU).

8. The method according to claim 1, wherein the amino acids are canonical amino acids, non-canonical amino acids, amino acid derivatives, or a combination thereof.

9. A modified peptide comprising:

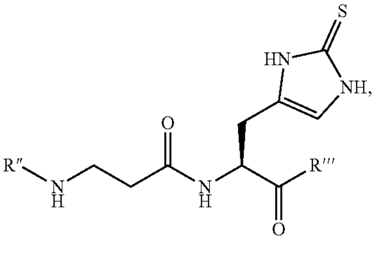

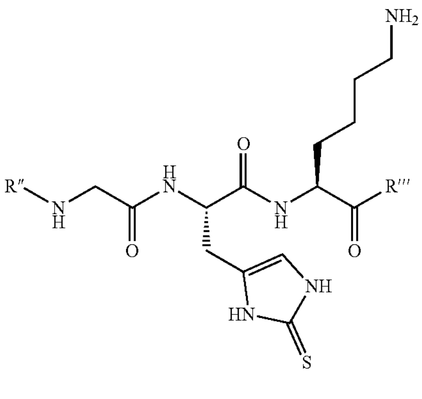

, or

-continued

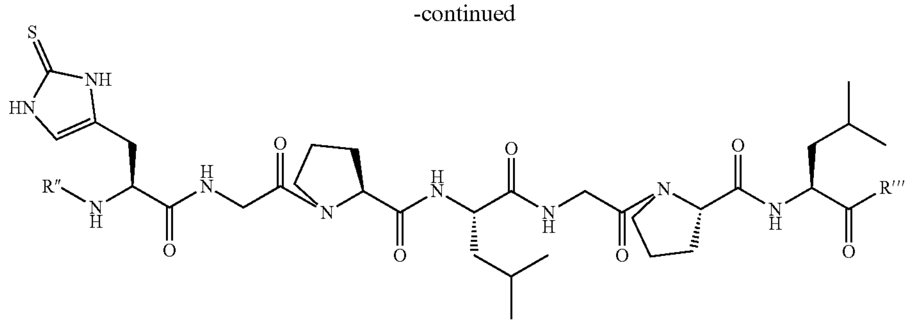

(SEQ ID NO:1, where His is replaced with 2-thioHis), wherein is a R" is H, a capping group, a linking group, a peptide group, or a linking group covalently bonded to a capping group and R''' is —OH, —$NH_2$, —OR'''', where R'''' is an alkyl group.

10. The modified peptide according to claim 9, wherein the peptide has the following structure:

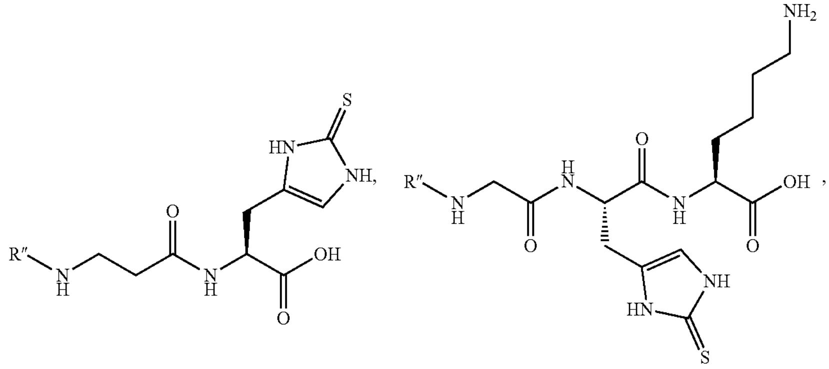

, or

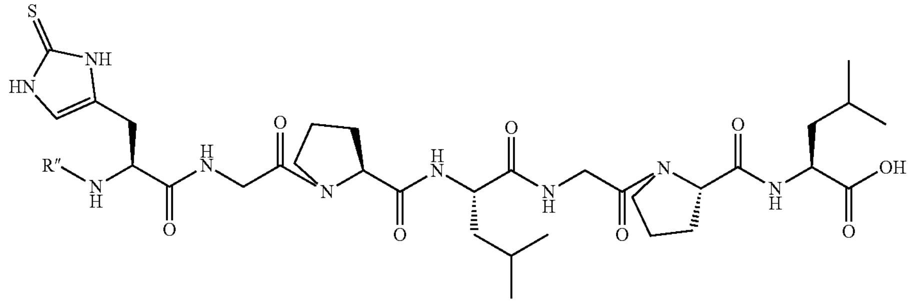

(SEQ ID NO:1, where His is replaced with 2-thioHis).

11. The modified peptide according to claim 9, wherein the capping group is an acetyl group, a palmitoyl group, or an ascorbic acid group.

12. The modified peptide according to claim 9, wherein the linking group is a succinyl group, a polyethylene glycol group, or a combination thereof.

13. The modified peptide according to claim 9, wherein the peptide has the following structure:

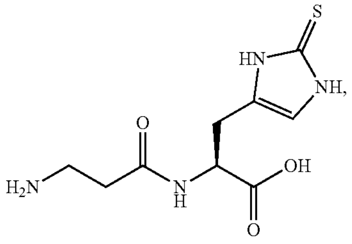
,
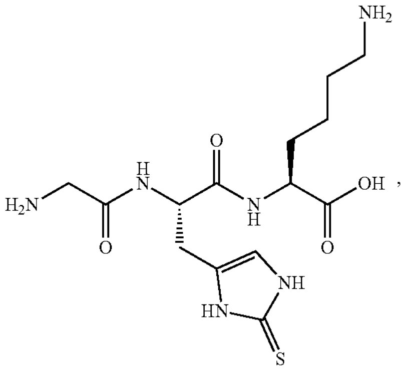
, or

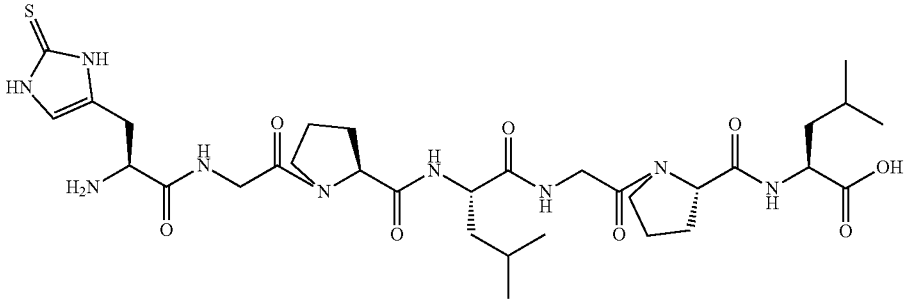

(SEQ ID NO:1, where His is replaced with 2-thioHis).

14. A composition comprising a modified peptide according to claim 9 and a carrier.

15. The composition of claim 14, wherein the composition is a cosmetic composition.

16. The composition of claim 15, wherein the cosmetic composition is a skin care product.

17. A method for scavenging metals or radicals, comprising contacting a solution or medium comprising metals or radicals with a modified peptide of according to claim 9 or a composition comprising the modified peptide, wherein the metals or radicals bind to the modified peptide.

18. A method for decreasing oxidative stress in an individual in need of treatment comprising administering to an individual a therapeutically effective amount of a modified peptide according to claim 9 or a composition comprising the modified peptide, wherein the oxidative stress of the individual is decreased.

* * * * *